US009588210B2

(12) United States Patent
Tsukada et al.

(10) Patent No.: US 9,588,210 B2
(45) Date of Patent: Mar. 7, 2017

(54) ANALYSIS APPARATUS, ANALYSIS METHOD AND ANALYSIS SYSTEM

(75) Inventors: Masashi Tsukada, Kyoto (JP); Yasuhide Kusaka, Kyoto (JP)

(73) Assignee: ARKRAY, Inc., Kyoto (JP)

(*) Notice: Subject to any disclaimer, the term of this patent is extended or adjusted under 35 U.S.C. 154(b) by 734 days.

(21) Appl. No.: 13/581,152

(22) PCT Filed: Feb. 1, 2011

(86) PCT No.: PCT/JP2011/052018
§ 371 (c)(1),
(2), (4) Date: Sep. 13, 2012

(87) PCT Pub. No.: WO2011/105178
PCT Pub. Date: Sep. 1, 2011

(65) Prior Publication Data
US 2013/0197847 A1    Aug. 1, 2013

(30) Foreign Application Priority Data

Feb. 26, 2010 (JP) ................................. 2010-043102

(51) Int. Cl.
*G01R 35/00* (2006.01)
*A61B 5/1473* (2006.01)
*A61B 5/1486* (2006.01)
*G06F 19/10* (2011.01)
*A61B 5/1495* (2006.01)

(52) U.S. Cl.
CPC ............ *G01R 35/00* (2013.01); *A61B 5/1473* (2013.01); *A61B 5/1486* (2013.01); *A61B 5/1495* (2013.01); *G06F 19/10* (2013.01); *A61B 2560/0242* (2013.01)

(58) Field of Classification Search
CPC ............................. G01D 3/022; G01D 18/008
USPC ............................................................ 702/104
See application file for complete search history.

(56) References Cited

U.S. PATENT DOCUMENTS

| 6,248,067 | B1 | 6/2001 | Causey et al. | |
|---|---|---|---|---|
| 6,551,276 | B1 | 4/2003 | Mann et al. | |
| 6,554,798 | B1 | 4/2003 | Mann et al. | |
| 6,558,320 | B1 | 5/2003 | Causey et al. | |
| 6,560,471 | B1 * | 5/2003 | Heller et al. ................... | 600/347 |
| 6,576,117 | B1 * | 6/2003 | Iketaki ............... | G01N 27/3274 |
| | | | | 204/400 |

(Continued)

FOREIGN PATENT DOCUMENTS

CN        1908668 A      2/2007
JP        2003-502090    1/2003

(Continued)

OTHER PUBLICATIONS

International Search Report issued in International Application No. PCT/JP2011/052018 dated Mar. 15, 2011.

(Continued)

*Primary Examiner* — Manuel L Barbee
*Assistant Examiner* — Raymond Nimox
(74) *Attorney, Agent, or Firm* — Morgan, Lewis & Bockius LLP

(57) ABSTRACT

Provided is an analysis apparatus capable of acquiring a measurement result with high reliability that includes: a signal detection unit; a measuring unit; a first temperature detection unit; a second temperature detection unit; and a calculation unit.

15 Claims, 17 Drawing Sheets

(56) References Cited

U.S. PATENT DOCUMENTS

| | | |
|---|---|---|
| 6,641,533 B2 | 11/2003 | Causey et al. |
| 6,809,653 B1 | 10/2004 | Mann et al. |
| 6,872,200 B2 | 3/2005 | Mann et al. |
| 6,936,029 B2 | 8/2005 | Mann et al. |
| 6,979,326 B2 | 12/2005 | Mann et al. |
| 6,997,920 B2 | 2/2006 | Mann et al. |
| 7,025,743 B2 | 4/2006 | Mann et al. |
| 7,098,803 B2 | 8/2006 | Mann et al. |
| 7,109,878 B2 | 9/2006 | Mann et al. |
| 7,324,012 B2 | 1/2008 | Mann et al. |
| 7,351,323 B2 * | 4/2008 | Iketaki ............ C12Q 1/006 204/401 |
| 7,602,310 B2 | 10/2009 | Mann et al. |
| 7,815,602 B2 | 10/2010 | Mann et al. |
| 7,819,843 B2 | 10/2010 | Mann et al. |
| 2002/0002326 A1 | 1/2002 | Causey et al. |
| 2002/0014409 A1 * | 2/2002 | Matsumoto ....... C12Q 1/54 204/403.1 |
| 2002/0107476 A1 | 8/2002 | Mann et al. |
| 2003/0100821 A1 | 5/2003 | Heller et al. |
| 2003/0181851 A1 | 9/2003 | Mann et al. |
| 2003/0181852 A1 | 9/2003 | Mann et al. |
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0212364 A1 | 11/2003 | Mann et al. |
| 2004/0073095 A1 | 4/2004 | Causey et al. |
| 2004/0263354 A1 | 12/2004 | Mann et al. |
| 2005/0019219 A1 * | 1/2005 | Oshiman ............ G01K 1/16 422/82.12 |
| 2005/0171513 A1 | 8/2005 | Mann et al. |
| 2005/0239154 A1 | 10/2005 | Feldman et al. |
| 2006/0001550 A1 | 1/2006 | Mann et al. |
| 2006/0007017 A1 | 1/2006 | Mann et al. |
| 2006/0175206 A1 | 8/2006 | Miyazaki et al. |
| 2006/0175207 A1 * | 8/2006 | Miyazaki et al. ........ 205/777.5 |
| 2006/0202859 A1 | 9/2006 | Mastrototaro et al. |
| 2007/0074977 A1 * | 4/2007 | Guo ............ A61B 5/14532 205/792 |
| 2007/0156033 A1 | 7/2007 | Causey et al. |
| 2008/0030369 A1 | 2/2008 | Mann et al. |
| 2008/0033357 A1 | 2/2008 | Mann et al. |
| 2008/0086039 A1 | 4/2008 | Heller et al. |
| 2008/0086040 A1 | 4/2008 | Heller et al. |
| 2008/0086041 A1 | 4/2008 | Heller et al. |
| 2008/0086043 A1 | 4/2008 | Heller et al. |
| 2008/0091094 A1 | 4/2008 | Heller et al. |
| 2008/0091095 A1 | 4/2008 | Heller et al. |
| 2008/0147004 A1 | 6/2008 | Mann et al. |
| 2008/0147050 A1 | 6/2008 | Mann et al. |
| 2009/0301899 A1 * | 12/2009 | Hodges ............ G01N 27/3274 205/777.5 |
| 2009/0325205 A1 * | 12/2009 | Fujii ............ C12Q 1/006 435/14 |
| 2011/0174638 A1 | 7/2011 | Katsuki et al. |
| 2012/0116706 A1 | 5/2012 | Nakanishi et al. |
| 2012/0179015 A1 | 7/2012 | Mann et al. |
| 2012/0316412 A1 | 12/2012 | Heller et al. |
| 2013/0324940 A1 | 12/2013 | Mann et al. |
| 2013/0324941 A1 | 12/2013 | Mann et al. |
| 2013/0345625 A1 | 12/2013 | Causey, III et al. |

FOREIGN PATENT DOCUMENTS

| | | |
|---|---|---|
| JP | 2007-203092 | 8/2007 |
| JP | 2009-258129 | 11/2009 |
| JP | H06-258129 | 11/2009 |
| JP | 2011-167503 | 9/2011 |
| WO | 00/78210 A1 | 12/2000 |
| WO | WO 2011/001917 | 6/2011 |

OTHER PUBLICATIONS

International Preliminary Report on Patentability and Written Opinion issued in corresponding International Application No. PCT/JP2011/052018 mailed Sep. 27, 2012.

Office Action issued in counterpart Chinese Patent Application No. 201180011040.0 dated Feb. 25, 2014.

Extended European Search Report issued in corresponding European Patent Application No. 11747142.5 dated Nov. 7, 2014.

Kost et al., "pH Standardization for Phosphorus-31 Magnetic Resonance Heart Spectroscopy at Different Temperatures," Magnetic Resonance in Medicine, 14: 496-506 (1990).

* cited by examiner

ANALYSIS APPARATUS, ANALYSIS METHOD AND ANALYSIS SYSTEM

CROSS-REFERENCE TO RELATED APPLICATION

This application is the U.S. National Phase under 35 U.S.C. §371 of International Application PCT/JP2011/052018, filed on Feb. 1, 2011, which claims priority to JP Application No. 2010-043102 filed on Feb. 26 2010, the contents of which are herein incorporated by reference in their entireties.

TECHNICAL FIELD

The present invention relates to an analysis apparatus, an analysis method and an analysis system to calculate numerical value information on a specified substance in a sample.

BACKGROUND OF THE INVENTION

A conventional method of measuring a blood sugar level is exemplified by a method of measuring the blood sampled from a fingertip and so forth by use of a puncture instrument with a disposable test piece on which a dried reagent containing an enzyme is placed (e.g., Patent document 2). There is a method of measuring a glucose concentration not in the blood but in an extracellular fluid (interstitial fluid) by making use of a sensor that is subcutaneously inserted (e.g., Patent document 1).

An electrochemical sensor for detecting a specified component in a sample by making use of enzyme reaction in away that immobilizes the enzyme to a subcutaneously detained sensor unit is employed as the sensor for measuring the glucose concentration in some cases. The electrochemical sensor normally includes a working electrode and a counter electrode, in which the enzyme (e.g., a glucose oxidase) is immobilized to the working electrode. The glucose concentration is measured based on a response current acquired by continuously applying a fixed voltage (e.g., about 0.3V-0.6V) to between the working electrode and the counter electrode.

The blood sugar level (a value of the glucose concentration in the blood) is different from a value of the glucose concentration in the interstitial fluid, and it is therefore necessary to correct the value of the glucose concentration in the interstitial fluid. As a method of correcting the value of the glucose concentration in the interstitial fluid, there is a method of calibrating the value to a value of the glucose concentration in the blood from a response current value acquired due to reaction between the interstitial fluid and the enzyme by use of the value of the glucose concentration in the blood that is obtained from measurement of the sampled blood.

An activity of the enzyme fluctuates depending on a reaction temperature. A subcutaneous temperature largely fluctuates depending on a change in temperature condition ambient to an examinee such as a living environment (e.g., an outdoor air temperature) of the examinee and activities in daily living (such as bathing and taking excises) thereof. In the case of continuously measuring the glucose concentration by the subcutaneous-detention type electrochemical sensor, a measurement result thereof is affected by the fluctuation in subcutaneous temperature as the case may be. Further, in the case of measuring the glucose concentration in the blood by using the sampled blood also, the measurement result is affected by the fluctuation in subcutaneous temperature as the case may be.

Patent document 1: U.S. Pat. No. 6,560,471
Patent document 2: Japanese Examined Patent Application Publication No. 06-58338

SUMMARY OF THE INVENTION

Problems

If the ambient temperature when measuring the response current by employing the subcutaneous-detention type electrochemical sensor is coincident with the ambient temperature when measuring the glucose concentration in the blood by sampling the blood, the value of the glucose concentration in the interstitial fluid can be properly corrected. Whereas if a difference between the ambient temperature when measuring the response current by employing the subcutaneous-detention type electrochemical sensor and the ambient temperature when measuring the glucose concentration in the blood by sampling the blood exceeds an allowable range, however, it is hard to properly correct the value of the glucose concentration in the interstitial fluid. It is an object of the present invention, which was devised under such circumstances, to provide a technology capable of acquiring a measurement result with high reliability under a condition exhibiting a large fluctuation in ambient temperature when measuring numerical value information on a specified substance in a sample.

The present invention adopts the following means in order to solve the problems given above. Namely, an analysis apparatus according to the present invention includes: a signal detection unit to continuously detect signal values detected from a first sample; a measuring unit to measure numerical value information on a specified substance in a second sample; a first temperature detection unit to capture a first temperature value defined as temperature information on the first sample; a second temperature detection unit to capture a second temperature value defined as temperature information on the second sample; and a calculation unit to calibrate to the numerical value information on the specified substance in the first sample from the signal value by referring to the numerical value information on the specified substance in the second sample in accordance with the first temperature value and the second temperature value.

The calculation unit calibrates to the numerical value information on the specified substance in the first sample from the signal value detected from the first sample by referring to the numerical value information on the specified substance in the second sample in accordance with the first temperature value and the second temperature value. Accordingly, even if the temperature pertaining to the first sample largely fluctuates and if the temperature pertaining to the second sample largely fluctuates, it is feasible to improve reliability on the numerical value information about the specified substance in the first sample.

The calculation unit may, when the value calculated from the first temperature value and the second temperature value is equal to or smaller than a predetermined threshold value, calibrate to the numerical value information on the specified substance in the first sample from the signal value by referring to the numerical value information on the specified substance in the second sample. Accordingly, even if the temperature pertaining to the first sample largely fluctuates and if the temperature pertaining to the second sample largely fluctuates, it is feasible to improve reliability on the numerical value information about the specified substance in the first sample.

The calculation unit may change the first temperature value when a value calculated from the first temperature value and the second temperature value exceeds a predetermined threshold value, correct the signal value detected from the first sample on the basis of the post-changed first temperature value when a value calculated from the post-changed first temperature value and the second temperature value is equal to or smaller than the predetermined threshold value, and calibrate to the numerical value information on the specified substance in the first sample from the post-corrected signal value by referring to the numerical value information on the specified substance in the second sample. Therefore, even if the temperature pertaining to the first sample largely fluctuates and if the temperature pertaining to the second sample largely fluctuates, it is possible to improve the reliability on the numerical value information about the specified substance in the first sample by changing the first temperature value defined as the temperature information related to the first sample.

The calculation unit may change the second temperature value when a value calculated from the first temperature value and the second temperature value exceeds the predetermined threshold value, correct the numerical value information on the specified substance in the second sample on the basis of the post-changed second temperature value when a value calculated from the first temperature value and the post-changed second temperature value is equal to or smaller than the predetermined threshold value, and calibrate to the numerical value information on the specified substance in the first sample from the signal value by referring to the post-corrected numerical value information on the specified substance in the second sample. Therefore, even if the temperature pertaining to the first sample largely fluctuates and if the temperature pertaining to the second sample largely fluctuates, it is possible to improve the reliability on the numerical value information about the specified substance in the first sample by changing the second temperature value defined as the temperature information related to the second sample.

The calculation unit may change the first temperature value and the second temperature value when a value calculated from the first temperature value and the second temperature value exceeds the predetermined threshold value, correct the signal value detected from the first sample on the basis of the post-changed first temperature value when a value calculated from the post-changed first temperature value and the post-changed second temperature value is equal to or smaller than the predetermined threshold value, further correct the numerical value information on the specified substance in the second sample on the basis of the post-changed second temperature value, and calibrate to the numerical value information on the specified substance in the first sample from the post-corrected signal value by referring to the post-corrected numerical value information on the specified substance in the second sample. Accordingly, even if the temperature pertaining to the first sample largely fluctuates and if the temperature pertaining to the second sample largely fluctuates, it is possible to improve the reliability on the numerical value information about the specified substance in the first sample by changing the first temperature value defined as the temperature information on the first sample and changing the second temperature value defined as the temperature information on the second sample.

Moreover, the analysis apparatus according to the present invention may further include a notifying unit to notify of predetermined information when a value calculated from the first temperature value and the second temperature value exceeds the predetermined threshold value. In addition, the analysis apparatus according to the present invention may further include a display unit to display the numerical value information on the specified substance in the first sample. The display unit may not display, when a value calculated from the first temperature value and the second temperature value exceeds the predetermined threshold value, the post calibrated numerical value information on the specified substance in the first sample. The signal detection unit may be detained within a body. The first temperature detection unit may be disposed between the signal detection unit and the surface of a skin. The value calculated by the calculation unit from the first temperature value and the second temperature value may be a difference value between the first temperature value and the second temperature value. The value calculated by the calculation unit from the first temperature value and the second temperature value may also be the larger value of a difference value between a variation quantity of the first temperature value per unit time and a variation quantity of the second temperature value per unit time and a difference value between an average value of the first temperature values and an average value of the second temperature values.

Furthermore, the present invention can be also grasped as an analysis method or an analysis system. That is, the analysis method according to the present invention includes: a signal detecting step of continuously detecting signal values detected from a first sample; a measuring step of measuring numerical value information on a specified substance in a second sample; a first temperature detecting step of capturing a first temperature value defined as temperature information on the first sample; a second temperature detecting step of capturing a second temperature value defined as temperature information on the second sample; and a calculating step of calibrating to the numerical value information on the specified substance in the first sample from the signal value by referring to the numerical value information on the specified substance in the second sample in accordance with the first temperature value and the second temperature value.

Moreover, the analysis method according to the present invention may further include a notifying step of notifying of predetermined information when a value calculated from the first temperature value and the second temperature value exceeds the predetermined threshold value. Additionally, the analysis method according to the present invention may further include a displaying step of displaying the numerical value information on the specified substance in the first sample. The displaying step may not include displaying, when a value calculated from the first temperature value and the second temperature value exceeds the predetermined threshold value, the post calibrated numerical value information on the specified substance in the first sample. The signal detecting step may be executed by a signal detection unit detained within a body. The first temperature detecting step may be executed by the first temperature detection unit disposed between the signal detection unit and the surface of a skin. The value calculated in the calculating step from the first temperature value and the second temperature value may be a difference value between the first temperature value and the second temperature value. The value calculated in the calculating step from the first temperature value and the second temperature value may also be the larger value of a difference value between a variation quantity of the first temperature value per unit time and a variation quantity of the second temperature value per unit time and a difference value between an average value of the first temperature values and an average value of the second temperature values.

The analysis system according to the present invention includes: a detection device including a signal detection unit to continuously detect signal values detected from a first sample and a first temperature detection unit to capture a first temperature value defined as temperature information on the first sample; an analysis device including a measuring unit to measure numerical value information on a specified substance in a second sample; and a display device including a display unit to display the numerical value information on the specified substance in the first sample. The analysis system according to the present invention further includes: a second temperature detection unit to capture a second temperature value defined as temperature information on the second sample; and a calculation unit to calibrate to the numerical value information on the specified substance in the first sample from the signal value detected from the first sample by referring to the numerical value information on the specified substance in the second sample in accordance with the first temperature value and the second temperature value.

A program according to the present invention makes a computer execute: a signal detecting step of continuously detecting signal values detected from a first sample; a measuring step of measuring numerical value information on a specified substance in a second sample; a first temperature detecting step of capturing a first temperature value defined as temperature information on the first sample; a second temperature detecting step of capturing a second temperature value defined as temperature information on the second sample; and a calculating step of calibrating to the numerical value information on the specified substance in the first sample from the signal value by referring to the numerical value information on the specified substance in the second sample in accordance with the first temperature value and the second temperature value. A computer-readable recording medium according to the present invention may be a medium recorded with the program described above.

In the analysis system according to the present invention, the analysis device and the display device may be configured as one integral device or separate devices. Further, in the analysis system according to the present invention, the second temperature detection unit (s) may be provided in any one or both of the analysis device and the display device. Still further, the present invention may also be a program for getting the computer, other devices, machines, and so forth to realize any one of the functions. Yet further, the present invention may also be a non-transitory recording medium recorded with such a program that can be read by the computer and so forth.

Effects of the Invention

It is possible to acquire the measurement result with the high reliability under the condition exhibiting the large fluctuation in ambient temperature when measuring the numerical value information on the specified substance in the sample.

DETAILED DESCRIPTION OF THE INVENTION

An analysis system according to the present embodiment will hereinafter be described with reference to the drawings. Configurations in the following working examples are exemplifications, and the analysis system according to the embodiment is not limited to the configurations of the working examples.

First Working Example

Figure 1:
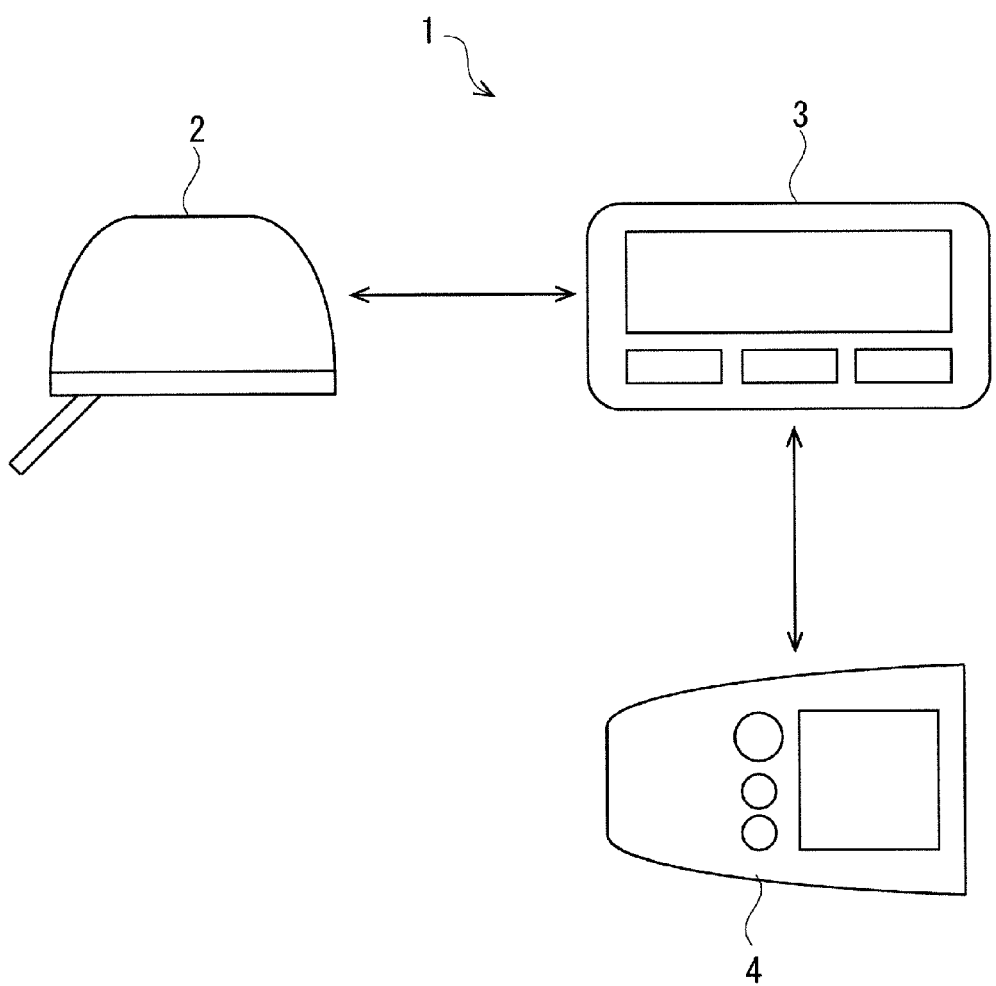
FIG. 1 is a schematic view of an architecture of an analysis system according to a first working example.

A first working example of the analysis system according to the embodiment will hereinafter be described. FIG. 1 is a schematic view of a configuration of an analysis system 1 according to the first working example. The analysis system 1 depicted in FIG. 1 includes a detection device 2, a display device 3 and a measuring device 4.

The detection device 2 is capable of continuously measuring a concentration of a specified substance in a sample in a body. The sample is exemplified by, e.g., a body fluid such as a blood and an interstitial fluid, and a matrix containing liquid other than the body fluid. The specified substance is exemplified by, e.g., glucose, a lactic acid, a bile acid, and so forth. In the present specification, the sample in the body is also referred to as a first sample. The detection device 2 can be used in a way of its being attached to, e.g., the skin of an abdomen region and a shoulder of a human body. The display device 3 can display a measurement result of the detection device 2. The detection device 2 and the display device 3 can perform wireless or wired data communications.

The measuring device 4 is capable of measuring the concentration of the specified substance in the sample taken out of the body. The sample is exemplified by, e.g., the body fluid such as the blood and the interstitial fluid, and the matrix containing liquid other than the body fluid. The specified substance is exemplified by, e.g., the glucose, the lactic acid, the bile acid, and so forth. In the present specification, the sample taken out of the body is also referred to as a second sample. The measuring device 4 is configured as a portable device that can be carried, and the display device 3 and the measuring device 4 can perform the wireless or wired data communications.

Figure 2:
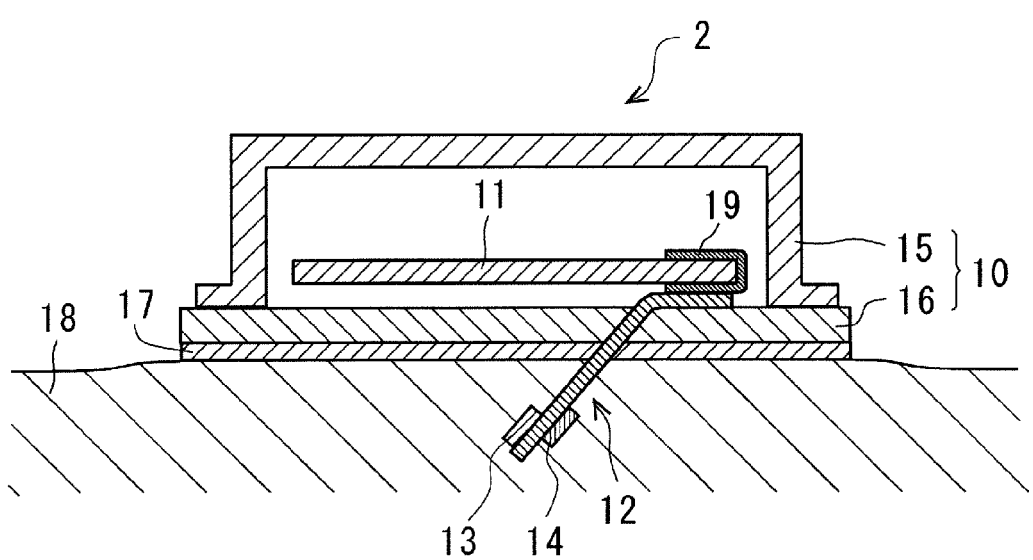
FIG. 2 is a schematic view of a configuration of a detection device 2 according to the first working example.

FIG. 2 is a schematic view of a configuration of the detection device 2 according to the first working example. The detection device 2 includes a housing 10, a circuit board 11, an electrochemical sensor 12, a signal detection unit 13 and a temperature detection unit 14. The housing 10 includes a cover 15 and a substrate 16. A space defined by the cover 15 and the substrate 16 accommodates the circuit board 11. It is preferable that the housing 10 has a water proofing property and a water resisting property. The cover 15 and the substrate 16 may involve using materials such as a metal and a polypropylene resin, which exhibit an extremely low level of water permeability.

The substrate 16 is a portion through which the electrochemical sensor 12 is inserted, and fixes a part of the electrochemical sensor 12. An adhesive film 17 is fixed to the substrate 16. The adhesive film 17 is used for fixing the detection device 2 to a skin 18. A tape having adhesion on both surfaces can be used as the adhesive film 17.

The circuit board 11 is mounted with electronic components such as a CPU (Central Processing Unit), a RAM (Random Access Memory) and a ROM (Read Only Memory) required for predetermined operations (such as applying a voltage and conducting the communications with the outside) of the detection device 2. The circuit board 11 includes a terminal 19 for establishing an electrical connection with the electrochemical sensor 12. The terminal 19 is used for applying the voltage to the signal detection unit 13 and obtaining a signal value (e.g., a response current value) from the signal detection unit 13.

A front end of the electrochemical sensor 12 is provided with the signal detection unit 13 and the temperature detection unit 14. A part of the electrochemical sensor 12 projects from the skin 18, abuts on the terminal 19 of the circuit board 11 and gets detained within the body (within the skin 18).

Figure 3:
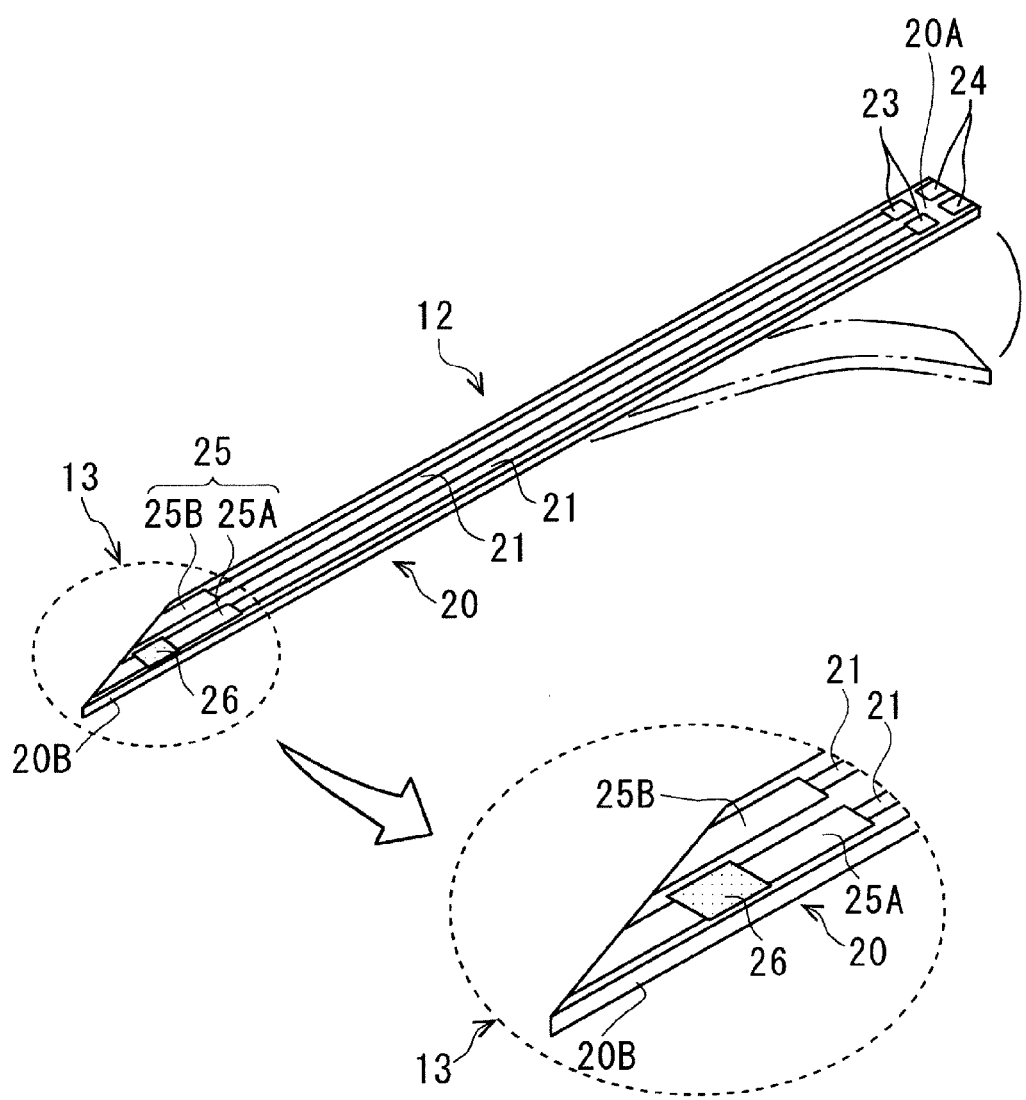
FIG. 3 is a perspective view of a whole electrochemical sensor 12 according to the first working example as well as being an enlarged view of a signal detection unit 13.
Figure 4:
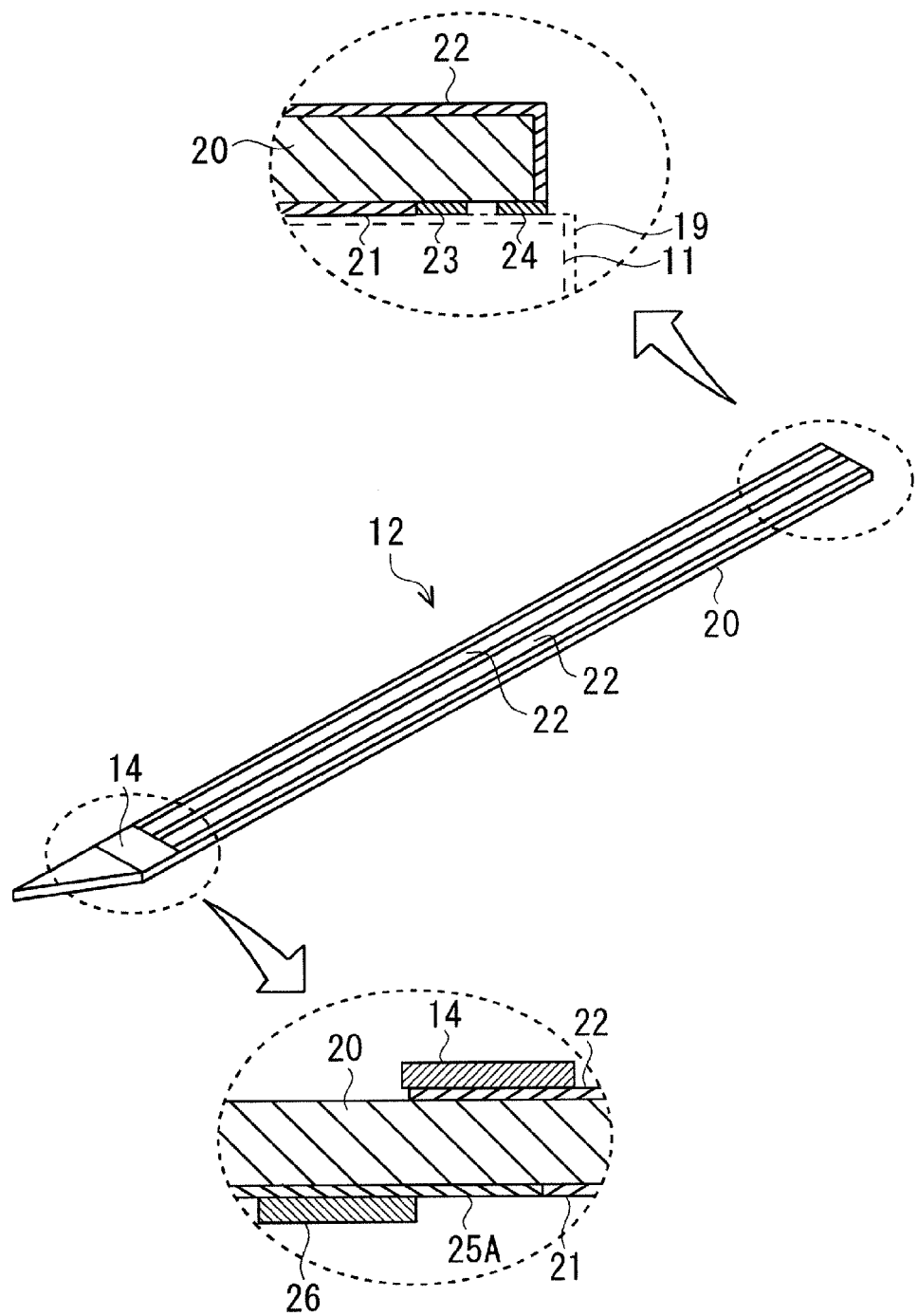
FIG. 4 is a perspective view of the whole electrochemical sensor 12 according to the first working example as well as being an enlarged view of the principal portion.

FIG. 3 illustrates a perspective view of the whole electrochemical sensor 12 and an enlarged view of the signal detection unit 13 according to the first working example. FIG. 4 illustrates the perspective view of the whole electrochemical sensor 12 and an enlarged view of the principal portion according to the first working example. The electrochemical sensor 12 includes the signal detection unit 13, the temperature detection unit 14, a substrate 20, lead wires 21, 22 and terminals 23, 24. The substrate 20 has an insulating property and flexibility. An edge 20A of the substrate 20 is accommodated in an interior of the housing 10. An edge of 20B of the substrate 20 is inserted into the skin 18. The edge of 20B of the substrate 20 may take an acute shape. The acute shape of the edge 20B of the substrate 20 can facilitate the insertion of the electrochemical sensor 12 into the skin 18, thereby making it possible to relieve a pain of an examinee whom the electrochemical sensor 12 is inserted into.

The substrate 20 can involve using a material having biocompatibility. For example, resins of polypropylene, polyimide, polyethylene terephthalate, polyether ether ketone and polyethylene naphthalate can be used as the substrate 20.

The signal detection unit 13 includes an electrode 25 and a reagent layer 26. The electrode 25 is formed on the upper surface of the substrate 20 and includes a working electrode 25A and a counter electrode 25B. The working electrode 25A is a portion which transfers and receives electrons to and from the specified substance in the first sample. The counter electrode 25B is used for applying the voltage together with the working electrode 25A. The electrode 25 can be formed based on screen printing that employs, e.g., a carbon ink.

The reagent layer 26 includes, e.g., an electron transfer substance and an oxidation-reduction enzyme. The reagent layer 26 can be formed by immobilizing the reagent layer 26 to the working electrode 25A on the upper surface of the substrate 20. In the case of measuring the concentration of the glucose in the first sample, e.g., glucose oxidase (GOD) or glucose dehydrogenase (GDH) can be used as the oxidation-reduction enzyme. In the case of measuring the concentration of the lactic acid in the first sample, for instance, lactate oxidase can be used as the oxidation-reduction enzyme. A method of immobilizing the oxidation-reduction enzyme can involve adopting multiple known methods, e.g., a method of making use of high polymer such as polymerizable gel, polyacrylamide and phosphor, MPC polymer produced by introducing a silane coupling agent into phospholipid polymer, or a protein film.

One edges of the lead wires 21 are connected to the working electrode 25A and the counter electrode 25B, and the other edges of the lead wires 21 are connected to the terminals 23. The lead wire 21 transfers information detected by the signal detection unit 13 to the circuit board 11. The terminal 23 of the substrate 20 is brought into contact with the terminal 19 of the circuit board 11.

The first sample abuts on the reagent layer 26, and the reagent layer 26 is dissolved by the first sample, at which time enzyme reaction starts. When applying the voltage to between the working electrode 25A and the counter electrode 25B, the specified substance in the first sample is reduced by the oxidation-reduction enzyme. Namely, the electrons are extracted from the specified substance in the first sample. The extracted electrons are supplied to the working electrode 25A via an electron medium substance. A quantity of electric charges of the electrons supplied to the working electrode 25A is detected as a response current by the signal detection unit 13. In the present specification, the response current detected by the signal detection unit 13 is also termed a first current. A first current value is continuously transferred to the circuit board 11 via the lead wires 21.

The temperature detection unit 14 is a sensor for detecting an ambient temperature in the vicinity of the signal detection unit 13 and is provided in a position vicinal to the signal detection unit 13 on the undersurface of the substrate 20. Further, the temperature detection unit 14 may also be provided in the position vicinal to the signal detection unit 13 on the upper surface of the substrate 20. The specified substance in the first sample undergoes the enzyme reaction on the reagent layer 26, and hence the ambient temperature in the vicinity of the signal detection unit 13 can be also called a temperature related to the first sample. In the present specification, the temperature information related to first sample is also referred to as a first temperature value. One edges of the lead wires 22 are connected to the temperature detection unit 14, and the other edges of the lead wires 22 are connected to terminals 24. The lead wire 22 transfers, to the circuit board 11, the first temperature value that is continuously detected by the temperature detection unit 14. A variety of known sensors in addition to, e.g., a thermistor can be used as the temperature detection unit 14.

The first working example demonstrates the instance of providing the temperature detection unit 14 in the position vicinal to the signal detection unit 13, however, the present embodiment is not limited to this instance. The temperature detection unit 14 may be provided between the signal detection unit 13 and the surface of the skin 18. The same position as a position in which the signal detection unit 13 is provided in a depthwise direction of the skin 18, is included between the signal detection unit 13 and the surface of the skin 18. Accordingly, the temperature detection unit 14 may also be provided in the same position as the position in which the signal detection unit 13 is provided in the depthwise direction of the skin 18. Further, the on-surface area of the skin 18 is embraced between the signal detection unit 13 and the surface of the skin 18. Therefore, the temperature detection unit 14 may also be provided on the surface of the skin 18. In the case of providing the temperature detection unit 14 on the surface of the skin 18, a temperature detected by the temperature detection unit 14 is approximately coincident with a surface temperature of the skin 18.

The first working example demonstrates the instance of providing the electrochemical sensor 12 with the temperature detection unit 14, however, the present embodiment is not limited to this instance. For example, the temperature detection unit 14 may also be disposed in a notched portion of the substrate 16, on the upper surface or the undersurface of the housing 10, on the upper surface or the undersurface of the circuit board 11, on the upper surface or the undersurface of the substrate 16, and so forth. Namely, the temperature detection unit 14 may be provided not on the electrochemical sensor 12 disposed outwardly of the detection device 2 but in an arbitrary position of the interior of the detection device 2.

Figure 5:
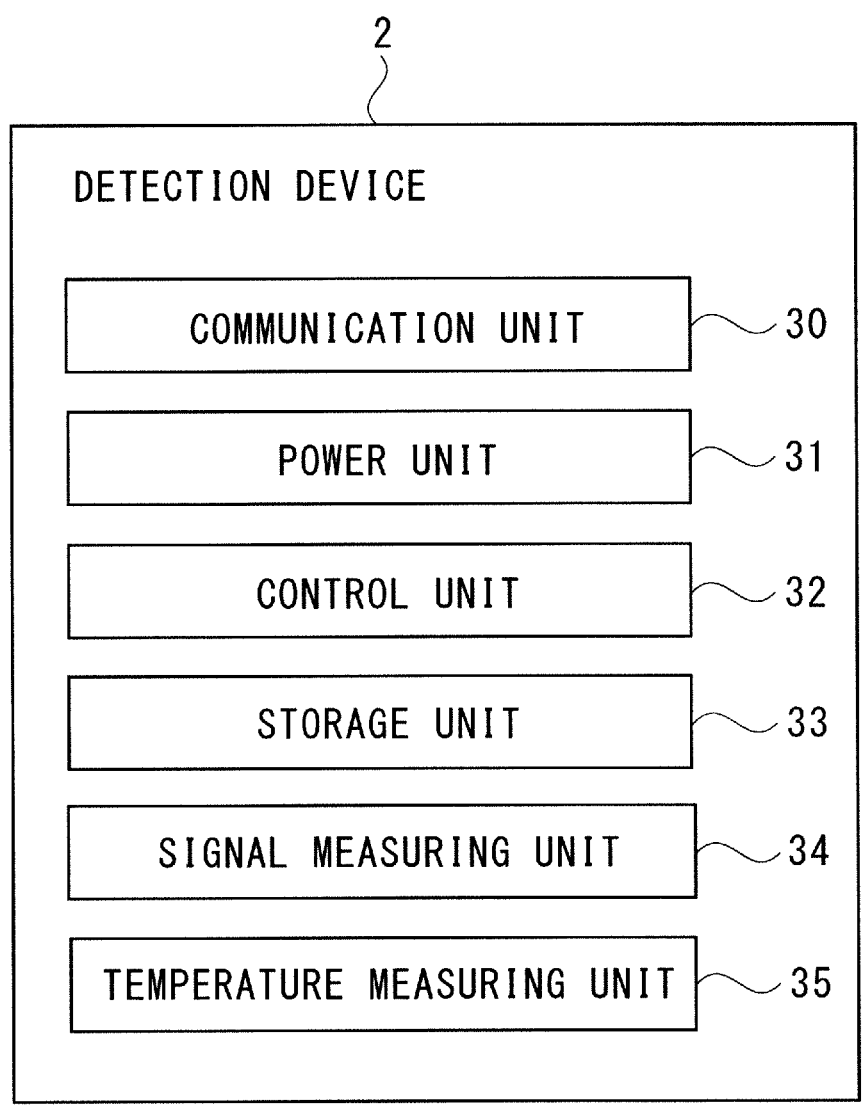
FIG. 5 is a diagram of a functional configuration of the detection device 2 according to the first working example.

Each of functions equipped in the detection device 2 will be described. FIG. 5 is a diagram of a functional configuration of the detection device 2 according to the first working example. The detection device 2 includes a communication unit 30, a power unit 31, a control unit 32, a storage unit 33, a signal measuring unit 34 and a temperature measuring unit 35.

The communication unit 30 performs the data communications between the detection device 2 and the display device 3. The data communications can involve making use of, e.g., wireless communication means (IrDA using infrared rays or Bluetooth using a frequency band of 2.4 GHz). Further, a connection between the detection device 2 and the display device 3 is established via a cable such as USB (Universal Serial Bus), whereby the wired data communications may also be conducted. The power unit 31 supplies the electric power for driving the detection device 2. For example, a function as the power unit 31 may be realized by employing a button battery of which a source voltage is 1V through 3V.

Figure 6A:
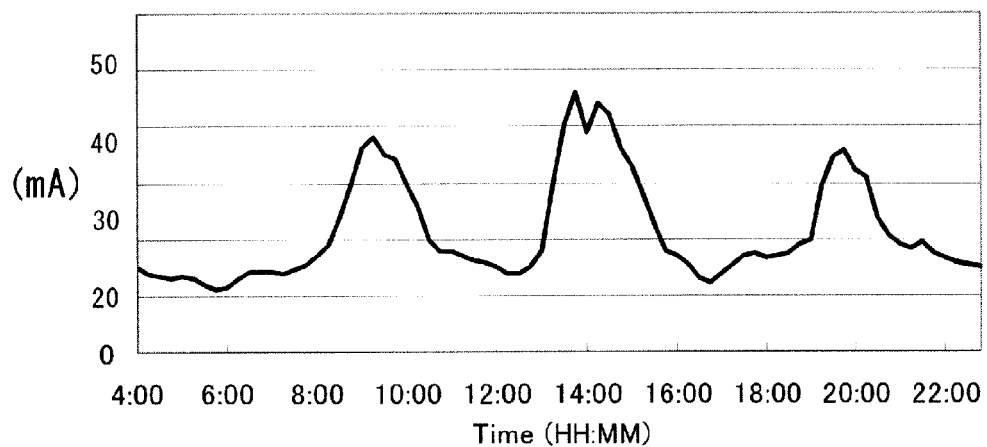
FIG. 6A illustrates graph data representing a variation in response current values that are continuously detected by a signal detection unit 13.

The control unit 32 controls, e.g., timing for applying the voltage, a value of the applied voltage, sampling of the response current or the communications with the display device 3. The storage unit 33 gets stored with programs needed for a variety of arithmetic operations, various items of data (e.g., data about a voltage applying pattern) and the like. The signal measuring unit 34 stores, in the storage unit 33, information on variations of the response current values that are continuously detected by the signal detection unit 13 together with elapsed time information. FIG. 6A illustrates graph data representing the variations of the response current values that are continuously detected by the signal detection unit 13. The axis of ordinates in FIG. 6A represents the response current value, while the axis of abscissas in FIG. 6A represents the elapsed time. The signal measuring unit 34 may store the graph data depicted in FIG. 6A in the storage unit 33. In the present specification, the information on the variations of the response current values that are continuously detected by the signal detection unit 13, is also referred to as variation information of the first current value.

Figure 6B:
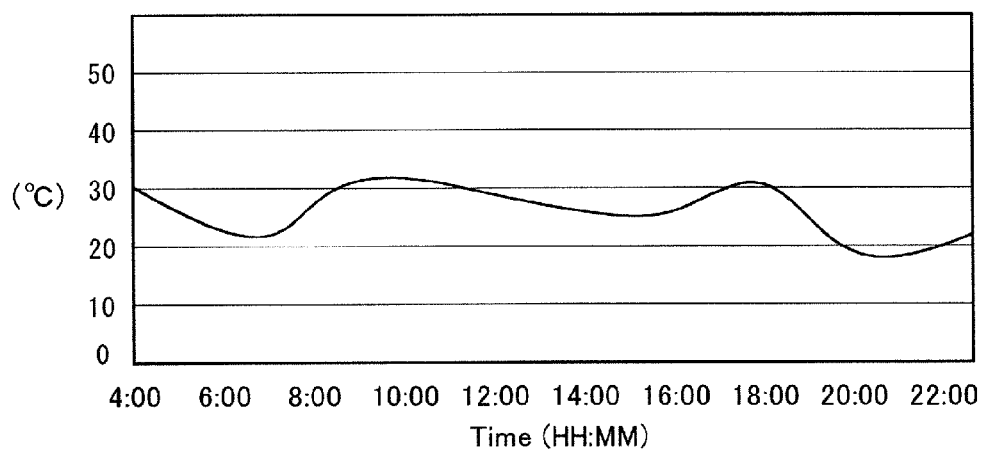
FIG. 6B illustrates graph data representing a variation in first temperature value detected by a temperature detection unit 14.

The temperature measuring unit 35 stores, in the storage unit 33, information on the variations of the first temperature value detected by the temperature detection unit 14 together with the elapsed time information. FIG. 6B illustrates graph data representing the variations of the first temperature value detected by the temperature detection unit 14. The axis of ordinates in FIG. 6B represents the first temperature value, while the axis of abscissas in FIG. 6B represents the elapsed time. The temperature measuring unit 35 may store the graph data illustrated in FIG. 6B in the storage unit 33. In the present specification, the information on the variations of the first temperature value detected by the temperature detection unit 14 is also termed variation information of the first temperature value.

The control unit 32, the storage unit 33, the signal measuring unit 34 and the temperature measuring unit 35 can be realized by a computer including the CPU, the RAM, the ROM and the like, by a variety of devices and by the programs and the like executed on the computer.

Figure 7:
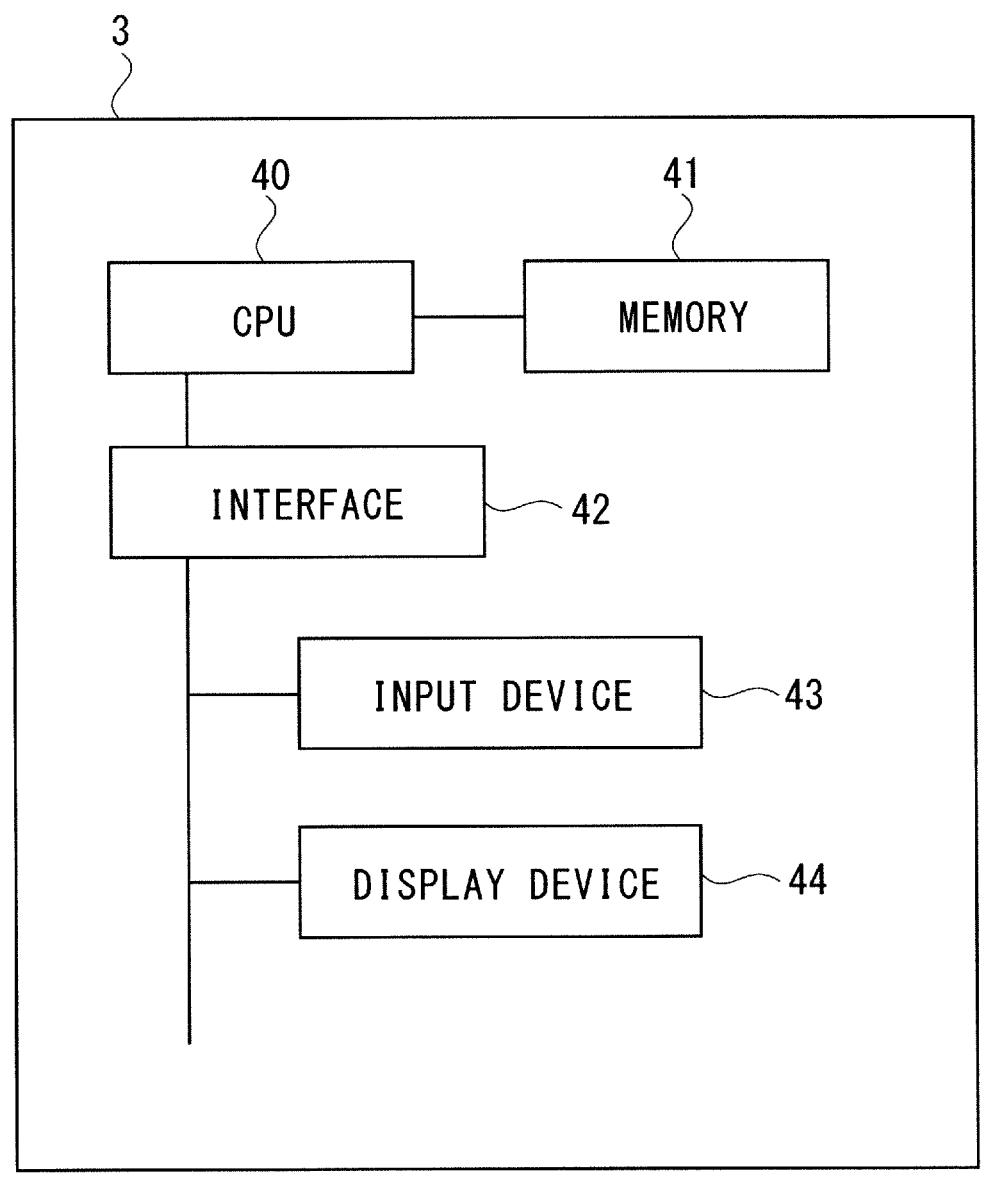
FIG. 7 is a schematic diagram of a configuration of a display device 3 according to the first working example.

FIG. 7 is a schematic diagram of a configuration of the display device 3 according to the first working example. The display device 3 includes: a CPU 40 which controls the display device 3 by executing the computer program; a memory 41 stored with the computer program executed by the CPU 40 and data processed by the CPU 40; an interface 42 which connects the CPU 40 to the variety of devices; an input device 43; and an output device 44.

The memory 41 is exemplified such as the RAM and the ROM. The interface 42 may be any one of a serial interface such as Universal Serial Bus (USB) and a parallel interface such as Peripheral Component Interconnect (PCI). The input device 43 is, e.g., an operation button and may also be a touch panel of touch-sensitive type. The output device 44 is, e.g., a liquid crystal display device, a plasma display panel, Cathode Ray Tube (CRT) or an electroluminescence panel, and so forth.

Figure 8:
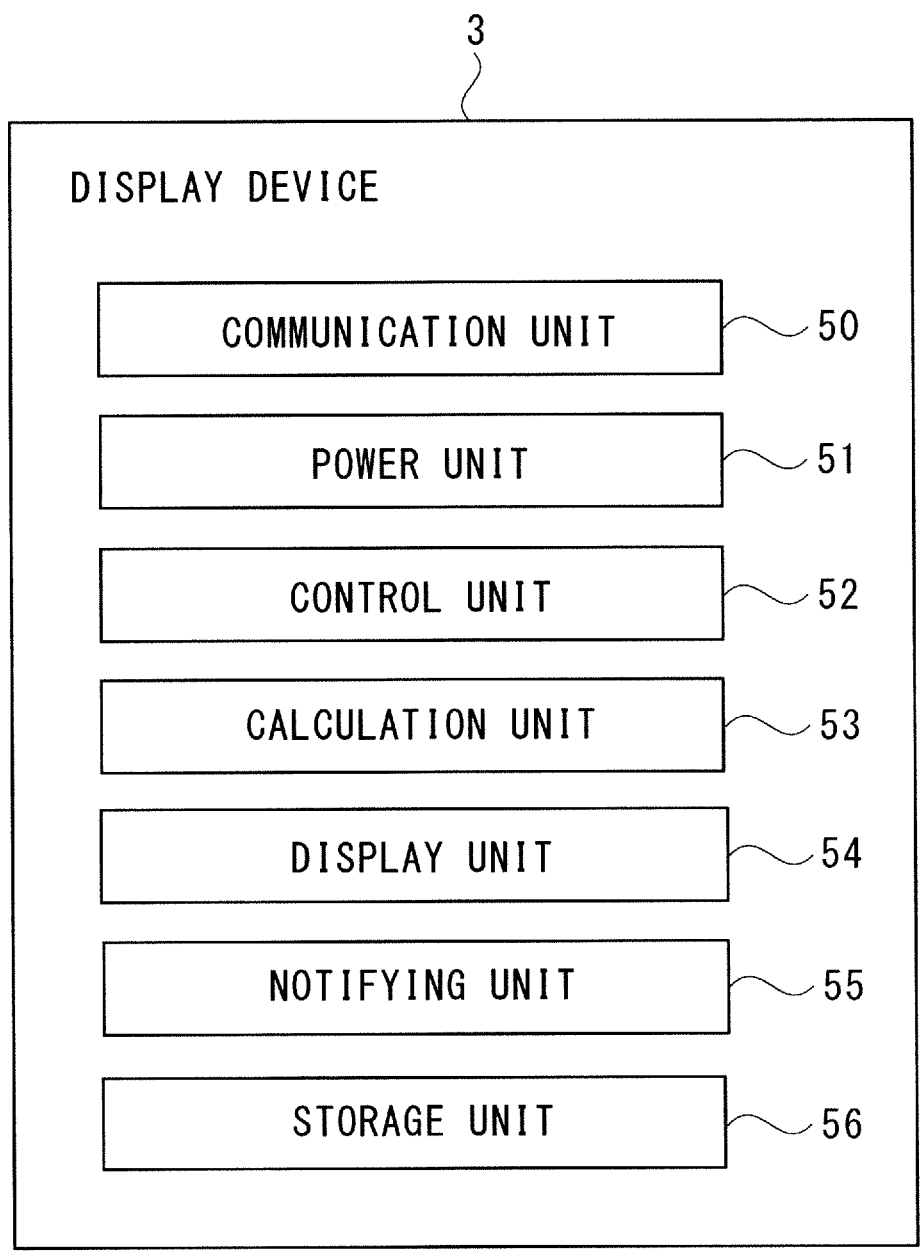
FIG. 8 is a diagram of a functional configuration of the display device 3 according to the first working example.

Each of functions equipped in the display device 3 will be described. FIG. 8 is a diagram of a functional configuration of the display device 3 according to the first working example. The display device 3 includes, a communication unit 50, a power unit 51, a control unit 52, a calculation unit 53, a display unit 54, a notifying unit 55 and a storage unit 56.

The communication unit 50 performs the data communications between the detection device 2 and the display device 3. Further, the communication unit 50 conducts the data communications between the display device 3 and the measuring device 4. The data communications can involve making use of, e.g., the wireless communication means (IrDA using the infrared rays or Bluetooth using the frequency band of 2.4 GHz). Moreover, the connection between the detection device 2 and the display device 3 is established via the cable such as USB (Universal Serial Bus), whereby the wired data communications may also be conducted.

The power unit 51 supplies the electric power for driving the display device 3. For instance, a function as the power unit 51 may be realized by using the button battery of which the source voltage is 1V through 3V. The control unit 52 controls, e.g., the communications with the detection device 2. The calculation unit 53 compares, e.g., the various items of data acquired from the detection device 2 with the various items of data acquired from the measuring device 4, and thus calculates a predetermined result.

The display unit 54 displays various items of information such as numerical value information on the specified substance in the first sample and numerical value information on the specified substance in the second sample. The numerical value information on the specified substance contains numerical value information for quantitatively evaluating the specified substance as in the case of a concentration and a quantity of the specified substance and numerical value information for qualitatively evaluating the specified substance. The display unit 54 can be realized by the computer including the CPU 40, the memory 41, the output device 44, and so forth, by each device and by the program and so forth executed on the computer. The notifying unit 55 gives notification of predetermined information.

The storage unit 56 gets stored with the programs required for the variety of arithmetic operations and the various items of data (e.g., the various items of data acquired from the detection device 2 and the various items of data acquired from the measuring device 4). The storage unit 56 is stored with calibration curve data representing a corresponding relation between the first current value and the concentration of the specified substance in the first sample. The calibration curve data are stored in the form of, e.g., a mathematical expression and a corresponding table in the storage unit 56. Further, plural sets of calibration curve data are prepared corresponding to the first temperature values, and the storage unit 56 is stored with the plural sets of calibration curve data corresponding to the first temperature values. The control unit 52, the calculation unit 53, the notifying unit 55 and the storage unit 56 can be realized by the computer including the CPU 40, the memory 41, and so forth, by the respective devices and by the programs and so forth executed on the computer.

Figure 9:
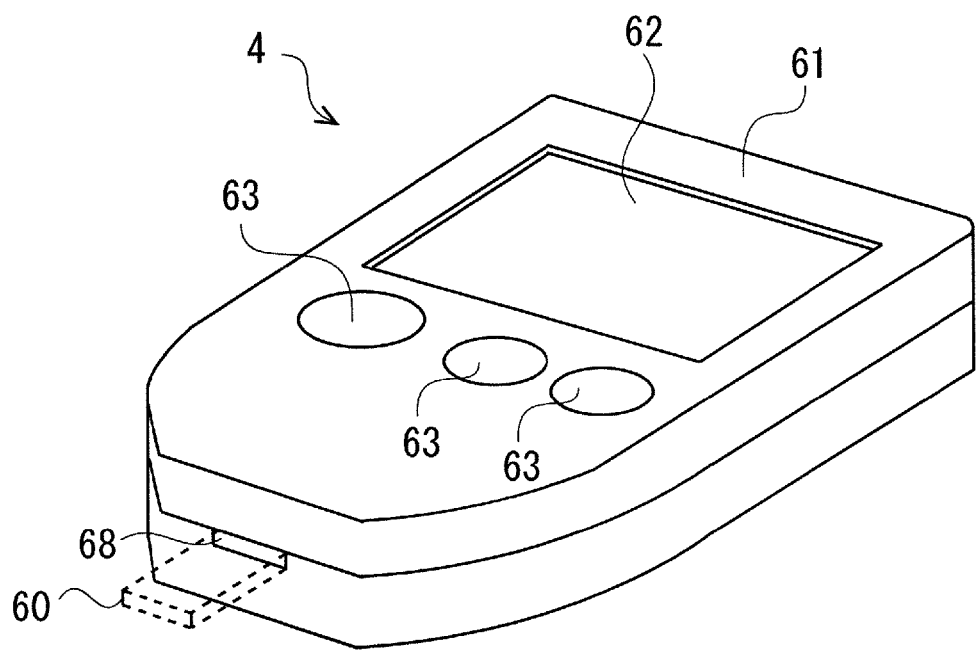
FIG. 9 is a schematic view of a configuration of a measuring device 4 according to the first working example.
Figure 10:
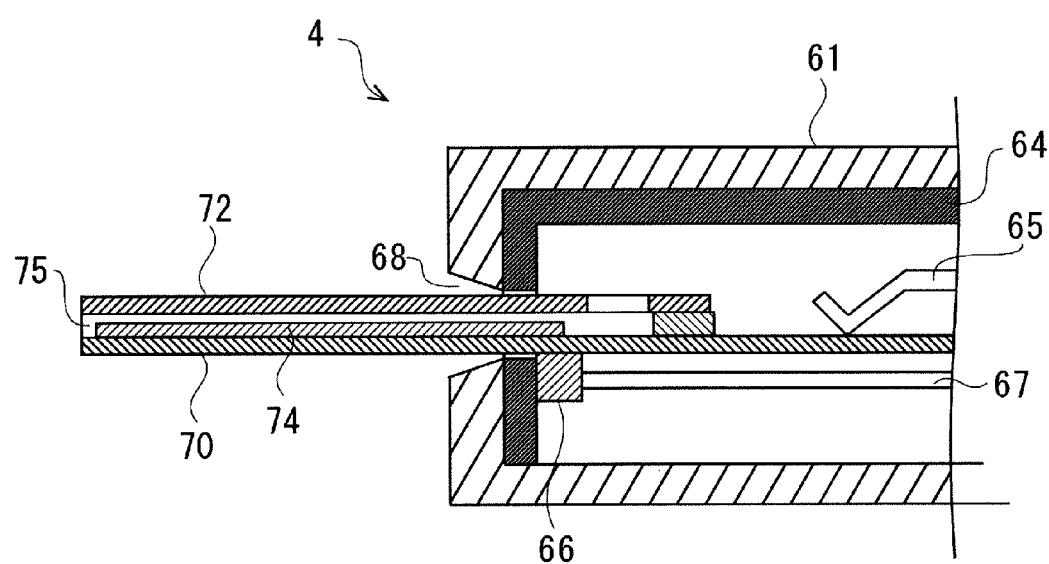
FIG. 10 is a partial sectional view of the measuring device 4 according to the first working example.

FIG. 9 is a schematic diagram of a configuration of the measuring device 4 according to the first working example. FIG. 10 is a partial sectional view of the measuring device 4 according to the first working example. The measuring device 4 measures the second sample on the basis of an electrochemical technique by use of a biosensor 60. The measuring device 4 includes a housing 61, a display panel 62, an operation button 63, a connector unit 64, a terminal 65, a temperature detection unit 66, a lead wire 67 and a sensor insertion port 68. Further, though an illustration is omitted, the measuring device 4 includes a circuit board mounted with the electronic components such as the CPU, the RAM and the ROM needed for the predetermined operations (such as applying the voltage and performing the communications with the outside) of the measuring device 4.

As depicted in FIG. 9, the housing 61 is provided with the display panel 62 and a plurality of operation buttons 63. The plurality of operation buttons 63 is used for making a variety of settings (such as setting a measurement condition and inputting an ID of the examinee), and carrying out the operations such as starting and finishing the measurement. The plurality of operation buttons 63 may also be the touch panel of the touch-sensitive type. The display panel 62 displays an operation procedure, an operation status, and so forth, at a time of setup as well as displaying a measurement result and an error. The display panel 62 is, for instance, the liquid crystal display device, the plasma display panel, Cathode Ray Tube (CRT) or the electroluminescence panel, and so forth.

Figure 11:
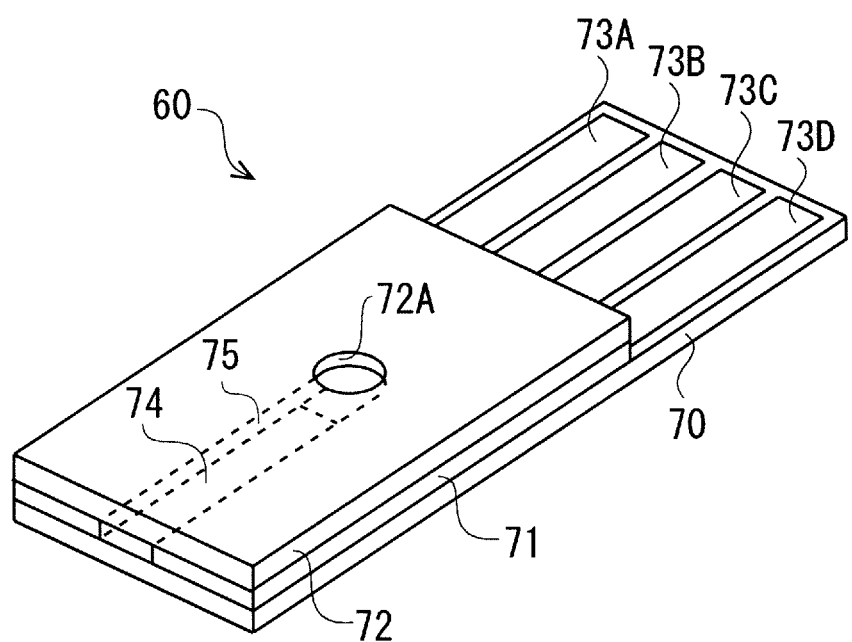
FIG. 11 is a perspective view of a whole biosensor 60 according to the first working example.

FIG. 11 is a perspective view of the whole biosensor 60 according to the first working example. The biosensor 60 includes a substrate 70, a spacer 71, a cover 72, electrodes 73A-73D and a reagent layer 74. The substrate 70 can involve using, e.g., an insulation resinous material. The electrodes 73A-73D are formed on the upper surface of the substrate 70 and include the working electrodes and the counter electrodes. The working electrode is a portion which transfers and receives the electrons to and from the specified substance in the second sample. The counter electrode is used for applying the voltage together with the working electrode. The electrodes 73A-73D can be formed based on the screen printing that employs, e.g., the carbon ink. A capillary 75 is formed inside the biosensor 60. The capillary 75 is provided with the reagent layer 74. The cover 72 includes an exhaust port 72A for discarding an internal gas of the capillary 75 to the outside. The capillary 75 moves the introduced second sample toward the exhaust port 72A of the cover 72 by capillary action. Further, the capillary 75 retains the introduced second sample.

The reagent layer 74 contains the electron transfer substance and the oxidation-reduction enzyme. The reagent layer 74 can be formed by immobilizing the reagent layer 74 to the working electrode on the upper surface of the substrate 70. In the case of measuring the concentration of the glucose in the second sample, e.g., glucose oxidase (GOD) or glucose dehydrogenase (GDH) can be used as the oxidation-reduction enzyme. In the case of measuring the concentration of the lactic acid in the second sample, for instance, lactate oxidase can be used as the oxidation-reduction enzyme. A method of immobilizing the oxidation-reduction enzyme can involve adopting multiple known methods, e.g., a method of making use of high polymer such as polymerizable gel, polyacrylamide and phosphor, MPC polymer produced by introducing a silane coupling agent into phospholipid polymer, or a protein film.

The temperature detection unit 66 is a sensor for measuring an ambient temperature in the vicinity of the reagent layer 74 in the biosensor 60. As illustrated in FIG. 10, the temperature detection unit 66 is provided in a position vicinal to the reagent layer 74 on the undersurface of the substrate 70 of the biosensor. The specified substance in the second sample into which the capillary 75 is introduced undergoes the enzyme reaction on the reagent layer 74, and hence the ambient temperature in the vicinity of the reagent layer 74 can be also called a temperature related to the second sample. In the present specification, the temperature information related to the second sample is also referred to as a second temperature value. One edges of the lead wires 67 are connected to the temperature detection unit 66, and the other edges of the lead wires 67 are connected to a circuit board. The lead wire 67 transfers, to the circuit board, the second temperature value detected by the temperature detection unit 66. A variety of known sensors in addition to, e.g., the thermistor can be used as the temperature detection unit 66.

Figure 12:
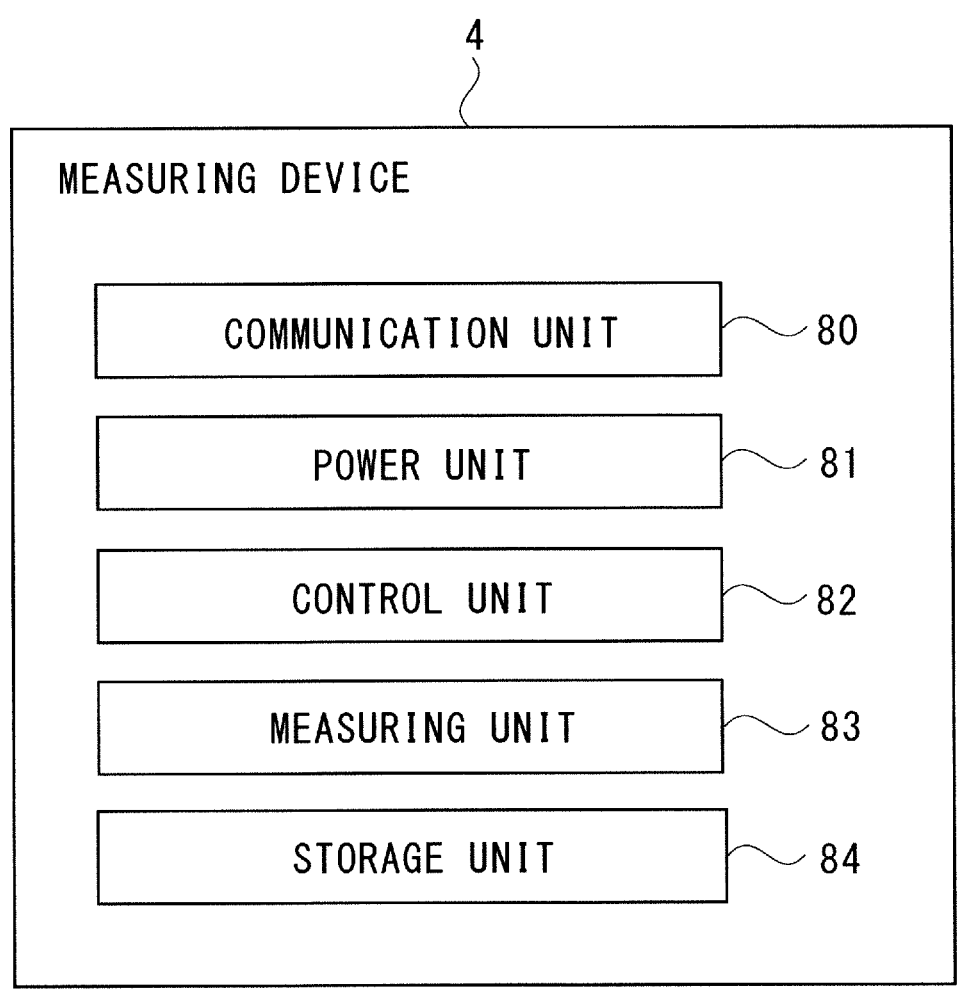
FIG. 12 is a diagram of a functional configuration of the measuring device 4 according to the first working example.

Each of functions equipped in the measuring device 4 will be described. FIG. 12 is a diagram of a functional configuration of the measuring device 4 according to the first working example. The measuring device 4 includes a communication unit 80, a power unit 81, a control unit 82, a measuring unit 83 and a storage unit 84.

The communication unit 80 performs the data communications between the display device 3 and the measuring device 4. The data communications can involve making use of, e.g., the wireless communication means (IrDA using the infrared rays or Bluetooth using the frequency band of 2.4 GHz). Further, the connection between the display device 3 and the measuring device 4 is established via the cable such as USB (Universal Serial Bus), whereby the wired data communications may also be conducted. The power unit 81 supplies the electric power for driving the measuring device 4. For example, a function as the power unit 81 may be realized by employing the button battery of which the source voltage is 1V through 3V. The control unit 82 controls the communications with, e.g., the detection device 2.

The measuring unit 83 measures the response current in the case of applying the voltage to the electrodes 73A-73D of the biosensor 60. The second sample introduced into the capillary 75 of the biosensor 60 is brought into contact with the reagent layer 74 provided on the capillary 75, and the reagent layer 74 is dissolved by the second sample introduced into the capillary 75, at which time the enzyme reaction starts.

As depicted in FIG. 10, when the biosensor 60 is attached to the connector unit 64, the electrodes 73A-73D of the biosensor 60 abut on the terminals 65, and the voltage is applied to the electrodes 73A-73D. When the voltage is applied to the working electrode and the counter electrode, the specified substance in the second sample is reduced by the oxidation-reduction enzyme. Namely, the electrons are extracted from the specified substance in the second sample that is introduced into the capillary 75. The extracted electrons are supplied to the working electrode via the electron medium substance. The measuring unit 83 measures a quantity of the electric charges of the electrons supplied to the working electrode as the response current. In the present specification, the response current measured by the measuring unit 83 is also termed a second current value. The measuring unit 83 stores the second current value in the storage unit 84. In this case, the measuring unit 83 stores the second current value in the storage unit 84 in a way that associates the second current value with time information of a point of time when measuring the second current.

The measuring unit 83 stores, in the storage unit 84, the second temperature value detected by the temperature detection unit 66. In this instance, the measuring unit 83 stores the second temperature value in the storage unit 84 by associating the second temperature value with the time information of the point of time when measuring the second current. That is, the measuring unit 83 stores, in the storage unit 84, the second temperature value given at the time when the second current is measured.

The storage unit 84 is stored with calibration curve data representing a corresponding relation between the second current value and the concentration of the specified substance in the second sample. The calibration curve data are stored in the form of, e.g., the mathematical expression and the corresponding table in the storage unit 84. Further, plural sets of calibration curve data are prepared corresponding to the second temperature values, and the storage unit 84 is stored with the plural sets of calibration curve data corresponding to the second temperature values.

The measuring unit 83 selects the calibration curve data corresponding to the second temperature value at the time when the second current is measured from within the plural sets of calibration curve data stored in the storage unit 84. Then, the measuring unit 83 applies the second current value to the selected calibration curve data, thereby measuring a concentration value of the specified substance in the second sample.

<Calibration Process>

A user of the system measures the first sample by employing the detection device 2, and measures the second sample by using the measuring device 4. The measurement result of the first sample is calibrated based on the measurement result of the second sample. The calibration of the measurement result of the first sample is carried out when the detection device 2 initially measures the first sample or while the detection device 2 continuously measures the first sample. To take into consideration a deviation between the measurement result of the first sample which is made by the detection device 2 and the measurement result of the second sample which is made by the measuring device 4, it is preferable that the calibration of the measurement result of the first sample is implemented once a day at the minimum. The system user operates the measuring device 4, and a calibration start signal is transmitted to the display device 3 from the measuring device 4, thereby starting the calibration of the measurement result of the first sample. Furthermore, the measuring device 4 may, when the second sample is introduced into the capillary 75 of the biosensor 60 and when the second current value is measured, transmit the calibration start signal to the display device 3.

Figure 13:
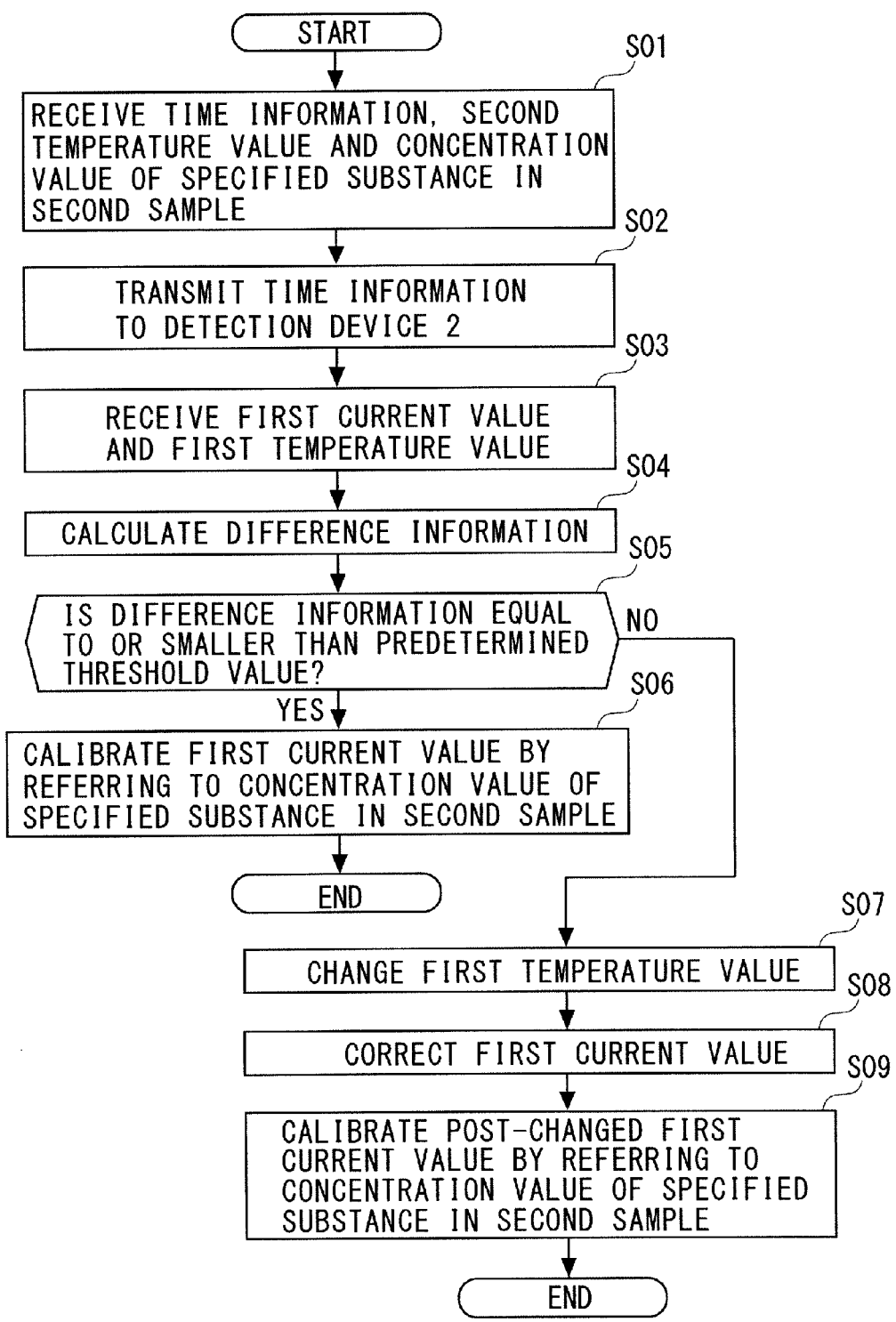
FIG. 13 is a flowchart illustrating a flow of a calibration process of a measurement result of a first sample.

FIG. 13 is a flowchart illustrating a flow of the calibration process of the measurement result of the first sample. The display device 3 receives the calibration start signal from the measuring device 4, which triggers the start of the flow depicted in FIG. 13. In step 01 of FIG. 13, the calculation unit 53 receives, from the measuring device 4 via the communication unit 50, the time information of the point of time when measuring the second current, the second temperature value at the time when the second current is measured and the concentration value of the specified substance in the second sample. Then, the calculation unit 53 stores, in the storage unit 56, the time information of the point of time when measuring the second current, the second temperature value at the time when the second current is measured and the concentration value of the specified substance in the second sample.

In step S02 of FIG. 13, the calculation unit 53 transmits the time information of the point of time when measuring the second current to the detection device 2 via the communication unit 50. The detection device 2 receives the time information of the point of time when measuring the second current. The detection device 2 extracts the first current value at the time when the second current is measured from variation information of the first current value that is stored in the storage unit 33. Further, the detection device 2 extracts the first temperature value at the time when the second current is measured from variation information of the first current value that is stored in the storage unit 33. The detection device 2 transmits, to the display device 3, the first current value at the time when the second current is measured and the first temperature value at the time when the second current is measured.

In step S03 of FIG. 13, the calculation unit 53 receives from the detection device 2 via the communication unit 50, the first current value at the time when the second current is measured and the first temperature value at the time when the second current is measured. Then, the calculation unit 53 stores, in the storage unit 56, the first current value at the time when the second current is measured and the first temperature value at the time when the second current is measured.

In step S04 of FIG. 13, the calculation unit 53 calculates difference information on the basis of the first temperature value at the time when the second current is measured and the second temperature value at the time when the second current is measured. The calculation unit 53 may also calculate, as the difference information, an absolute value of the difference between the first temperature value at the time when the second current is measured and the second temperature value at the time when the second current is measured. In the present specification, the absolute value of the difference between the first temperature value at the time when the second current is measured and the second temperature value at the time when the second current is measured, is also referred to as a first differential value.

Moreover, the calculation unit 53 receives a variation quantity of the first temperature value per unit time from the detection device 2 and also a variation quantity of the second temperature value per unit time from the measuring device 4, and may thereby calculate, as the difference information, the absolute value of the difference between the variation quantity of the first temperature value per unit time and the variation quantity of the second temperature value per unit time. In the present specification, the absolute value of the difference between the variation quantity of the first temperature value per unit time and the variation quantity of the second temperature value per unit time, is also termed a second differential value.

Further, the calculation unit 53 receives an average value of the first temperature values from the detection device 2 and also an average value of the second temperature values from the measuring device 4, and may thereby calculate, as the difference information, an absolute value of a difference between the average value of the first temperature values and the average value of the second temperature values. The average value of the first temperature values and the average value of the second temperature values may also be average values calculated on a minute or hour basis. In the present specification, the absolute value of the difference between the average value of the first temperature values and the average value of the second temperature values is also referred to as a third differential value.

Further, the calculation unit 53 may compare the second differential value with the third differential value. Then, the calculation unit 53 may calculate, as the difference information, the larger of the second differential value and the third differential value. That is, the calculation unit 53 selects the larger of the second differential value and the third differential value and may thereby calculate the selected larger value as the difference information.

In step S05 of FIG. 13, the calculation unit 53 determines whether or not the difference information is equal to or smaller than a predetermined threshold value. The predetermined threshold value is stored in the storage unit 56. The predetermined threshold value is an arbitrarily changeable value and can be set to, e.g., 5° C., 10° C. or 20° C., and so forth, however, the example is not limited to these values.

If the difference information is equal to or smaller than the predetermined threshold value (YES in step S05 of FIG. 13), the calculation unit 53 advances the processing to step S06 of FIG. 13. In step S06 of FIG. 13, the calculation unit 53 refers to the concentration value of the specified substance in the second sample and calibrates to the concentration value of the specified substance in the first sample from the first current value at the time when the second current is measured. In other words, the calculation unit 53 refers to the concentration value of the specified substance in the second sample and converts the first current value at the time when the second current is measured into the concentration value of the specified substance in the first sample.

Herein, an in-depth description of the calibration process by the calculation unit 53 in step S06 of FIG. 13 will be made. To start with, the calculation unit 53 selects the calibration curve data corresponding to the first temperature value at the time when the second current is measured from within the plural sets of calibration curve data stored in the storage unit 56. Then, the calculation unit 53 applies the first current value at the time when the second current is measured to the selected calibration curve data, thereby calculating the concentration value of the specified substance in the first sample.

Next, the calculation unit 53 modifies the post-calculated concentration value of the specified substance in the first sample by referring to the concentration value of the specified substance in the second sample. A value given when the concentration value of the specified substance in the first sample is indicated as a concentration value of the specified substance in the sample taken out of the body, is defined as a post-modified concentration value of the specified substance in the first sample. This is because the concentration value of the specified substance in the first sample represents the concentration value of the specified substance in the sample within the body, and it is required that the concentration value of the specified substance in the first sample is given as the concentration value of the specified substance in the sample taken out of the body. In the case of finishing the process in step S06 of FIG. 13, the processing flow depicted in FIG. 13 comes to an end.

On the other hand, if the difference information exceeds the predetermined threshold value (NO in step S05 of FIG. 13), the calculation unit 53 advances the processing to step S07 of FIG. 13. In step S07 of FIG. 13, the calculation unit 53 changes the first temperature value at the time when the second current is measured. In this case, the calculation unit 53 changes the first temperature value at the time when the second current is measured so that the absolute value of the difference between the post-changed first temperature value and the second temperature value at the time when the second current is measured becomes equal to or smaller than the predetermined threshold value.

For instance, the first temperature value at the time when the second current is measured is +30° C., the second temperature value at the time when the second current is measured is +20° C., and the predetermined threshold value is 8° C., in which case the absolute value (10° C.) of the difference between the first temperature value at the time when the second current is measured and the second temperature value at the time when the second current is measured, exceeds the predetermined threshold value. In this instance, the calculation unit 53 changes the first temperature value (+30° C.) at the time when the second current is measured to, e.g., +26° C. The absolute value (6° C.) of the difference between the post-changed first temperature value (+26° C.) and the second temperature value (+20° C.) at the time when the second current is measured, is equal to or smaller than the predetermined threshold value (8° C.). Note that if the absolute value of the difference between the post-changed first temperature value and the second temperature value at the time when the second current is measured, is equal to or smaller than the predetermined threshold value, the post-changed first temperature value may also be a value other than +26° C.

In step S08 of FIG. 13, the calculation unit 53 corrects, based on the post-changed first temperature value, the first current value at the time when the second current is measured. Herein, the correction of the first current value at the time when the second current is measured will be described. The storage unit 56 is stored with the data representing the corresponding relation between the first temperature value and the first current value. The calculation unit 53 extracts the first current value corresponding to the post-changed first temperature value from the data representing the corresponding relation between the first temperature value and the first current value. The calculation unit 53 uses the extracted first current value as the post-changed first current value.

In step S09 of FIG. 13, the calculation unit 53 refers to the concentration value of the specified substance in the second sample, and calibrates to the concentration value of the specified substance in the first sample from the post-changed first current value. Herein, the process in step S09 of FIG. 13 will be described in detail. At first, the calculation unit 53 selects the calibration curve data corresponding to the post-changed first temperature value from within the plural sets of calibration curve data stored in the storage unit 56. Then, the calculation unit 53 applies the post-changed first current value to the selected calibration curve data, thereby calculating the concentration value of the specified substance in the first sample. Next, the calculation unit 53 refers to the concentration value of the specified substance in the second sample, thereby modifying the post-calculated concentration value of the specified substance in the first sample. In the case of finishing the process in step S09 of FIG. 13, the processing flow illustrated in FIG. 13 is terminated. The processes from step S07 through step S09 of FIG. 13 are also termed the calibration process by the calculation unit 53 in the present specification.

The discussion made above demonstrates, in the processing flow depicted in FIG. 13, the example where if the difference information exceeds the predetermined threshold value (NO in step S05 of FIG. 13), the calculation unit 53 advances to the process in step S07 of FIG. 13. As a substitute for this operation, in the processing flow depicted in FIG. 13, if the difference information exceeds the predetermined threshold value (NO in step S05 of FIG. 13), the calculation unit 53 may finish the processing flow illustrated in FIG. 13 without advancing to the process in step S07 of FIG. 13. That is, in the processing flow depicted in FIG. 13, if the difference information exceeds the predetermined threshold value (NO in step S05 of FIG. 13), the calibration process by the calculation unit 53 may not be executed.

<First Modified Example of Calibration Process>

Figure 14:
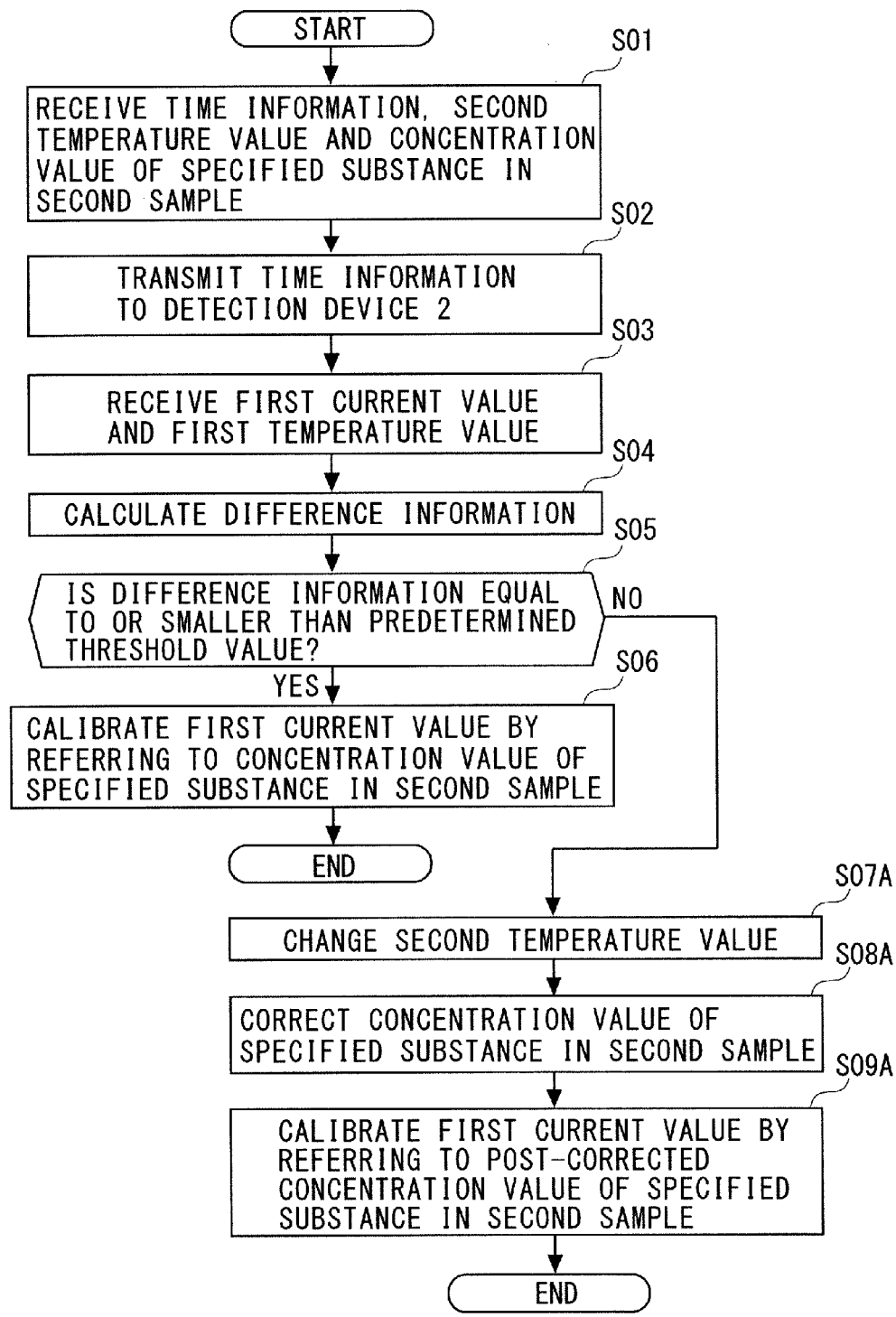
FIG. 14 is a flowchart illustrating a flow of the calibration process of the measurement result of the first sample.

Step S07, step S08 and step S09 of the processing flow illustrated in FIG. 13 may be modified as follows. FIG. 14 is a flowchart illustrating a flow of the calibration process of the measurement result of the first sample. In the processing flow depicted in FIG. 14, processes different from those in the processing flow illustrated in FIG. 13 are executed in step S07A, step S08A and step S09A. Such being the case, different points between FIG. 13 and FIG. 14 are described, and the same processes as those in the processing flow illustrated in FIG. 13 are marked with the same reference numerals as those in FIG. 13, while the detailed descriptions thereof are omitted. In the following discussion, the calculation unit 53 executes the processes in step S01 through step S05 of the processing flow illustrated in FIG. 14 and comes to a status of advancing to the process in step S07A of FIG. 14.

In step S07A of FIG. 14, the calculation unit 53 changes the second temperature value at the time when the second current is measured. In this instance, the calculation unit 53 changes the second temperature value at the time when the second current is measured so that the absolute value of the difference between the first temperature value at the time when the second current is measured and the post-changed second temperature value becomes equal to or smaller than the predetermined threshold value.

For example, the first temperature value at the time when the second current is measured is +22° C., the second temperature value at the time when the second current is measured is +32° C., and the predetermined threshold value is 8° C., in which case the absolute value (10° C.) of the difference between the first temperature value at the time when the second current is measured and the second temperature value at the time when the second current is measured, exceeds the predetermined threshold value. In this instance, the calculation unit 53 changes the second temperature value (+32° C.) at the time when the second current is measured to, e.g., +20° C. The absolute value (2° C.) of the difference between the first temperature value (+22° C.) at the time when the second current is measured and the post-changed second temperature value (+20° C.), is equal to or smaller than the predetermined threshold value (8° C.). Note that if the absolute value of the difference between the first temperature value at the time when the second current is measured and the post-changed second temperature value, is equal to or smaller than the predetermined threshold value, the post-changed second temperature value may also be a value excluding +20° C.

In step S08A of FIG. 14, the calculation unit 53 corrects the concentration value of the specified substance in the second sample on the basis of the post-changed second temperature value. Herein, the correction of the concentration value of the specified substance in the second sample will be explained. The storage unit 56 is stored with the calibration curve data representing the corresponding relation between the second current value and the concentration of the specified substance in the second sample. The calibration curve data are stored in the form of, e.g., the mathematical expression and the corresponding table in the storage unit 56. Further, the plural sets of calibration curve data are prepared corresponding to the second temperature values, and the storage unit 56 is stored with the plural sets of calibration curve data corresponding to the second temperature values.

The calculation unit 53 selects the calibration curve data corresponding to the post-changed second temperature value from within the plural sets of calibration curve data. Then, the calculation unit 53 applies the second current value to the selected calibration curve data, thereby calculating the concentration of the specified substance in the second sample. The calculation unit 53 uses the calculated concentration of the specified substance in the second sample as the post-corrected concentration of the specified substance in the second sample.

In step S09A of FIG. 14, the calculation unit 53 refers to the post-corrected concentration value of the specified substance in the second sample, and calibrates the first current value at the time when the second current is measured to the concentration value of the specified substance in the first sample. Herein, the process in step S09A of FIG. 14 will be described in detail. To begin with, the calculation unit 53 selects the calibration curve data corresponding to the first temperature value at the time when the second current is measured from within the plural sets of calibration curve data stored in the storage unit 56. Then, the calculation unit 53 calculates the concentration value of the specified substance in the first sample by applying the first current value at the time when the second current is measured to the selected calibration curve data.

Next, the calculation unit 53 modifies the post-calculated concentration value of the specified substance in the first sample in a way that refers to the concentration value of the specified substance in the second sample. In the case of finishing the process in step S09A of FIG. 14, the processing flow by the calculation unit 53 depicted in FIG. 14 comes to an end. The processes in step S07A through step S09A of FIG. 14 are also generically termed the calibration process by the calculation unit 53 in the present specification.

The discussion made above demonstrates, in the processing flow depicted in FIG. 14, the example where if the difference information exceeds the predetermined threshold value (NO in step S05 of FIG. 14), the calculation unit 53 advances to the process in step S07A of FIG. 14. In place of this operation, in the processing flow depicted in FIG. 14, if the difference information exceeds the predetermined threshold value (NO in step S05 of FIG. 14), the calculation unit 53 may finish the processing flow illustrated in FIG. 14 without advancing to the process in step S07A of FIG. 14. Namely, in the processing flow depicted in FIG. 14, if the difference information exceeds the predetermined threshold value (NO in step S05 of FIG. 14), the calibration process by the calculation unit 53 may not be executed.

<Second Modified Example of Calibration Process>

Figure 15:
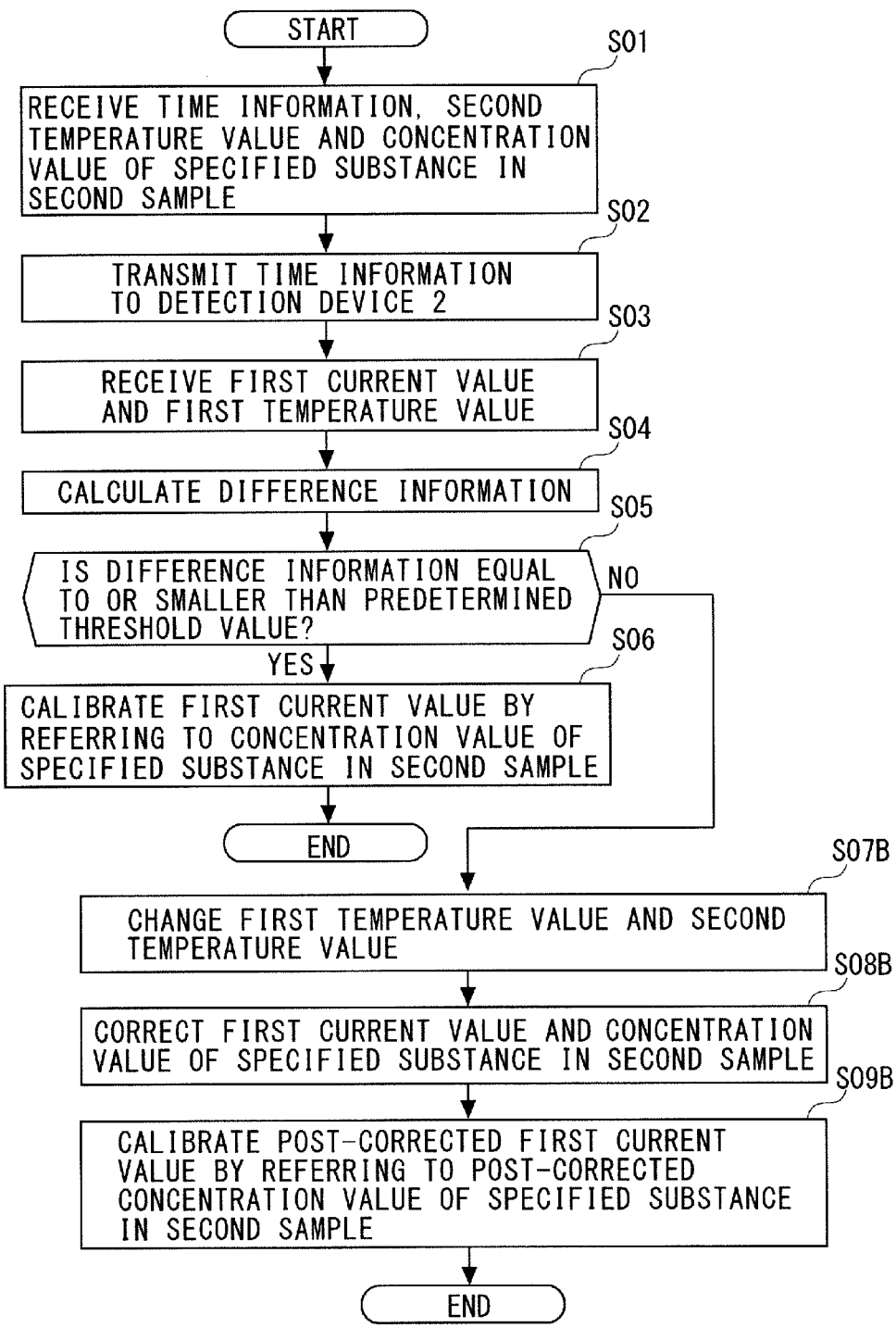
FIG. 15 is a flowchart illustrating a flow of the calibration process of the measurement result of the first sample.

Step S07, step S08 and step S09 of the processing flow illustrated in FIG. 13 may be modified as follows. FIG. 15 is a flowchart illustrating a flow of the calibration process of the measurement result of the first sample. In the processing flow depicted in FIG. 15, processes different from those in the processing flow illustrated in FIG. 13 are executed in step S07B, step S08B and step S09B. This being the case, different points between FIG. 13 and FIG. 15 are described, and the same processes as those in the processing flow illustrated in FIG. 13 are marked with the same reference numerals as those in FIG. 13, while the detailed descriptions thereof are omitted. In the following discussion, the calculation unit 53 executes the processes in step S01 through step S05 of the processing flow illustrated in FIG. 15 and comes to a status of advancing to the process in step S07B of FIG. 15.

In step S07B of FIG. 15, the calculation unit 53 changes the first temperature value at the time when the second current is measured and the second temperature values at the time when the second current is measured. In this case, the calculation unit 53 changes the first temperature value at the time when the second current is measured and the second temperature value at the time when the second current is measured so that the absolute value of the difference between the post-changed first temperature value and the post-changed second temperature value becomes equal to or smaller than the predetermined threshold value.

For example, the first temperature value at the time when the second current is measured is +22° C., the second temperature value at the time when the second current is measured is +34° C., and the predetermined threshold value is 8° C., in which case the absolute value (12° C.) of the difference between the first temperature value at the time when the second current is measured and the second temperature value at the time when the second current is measured, exceeds the predetermined threshold value. In this case, the calculation unit 53 changes the first temperature value (+22° C.) at the time when the second current is measured to, e.g., +24° C. and also changes the second temperature value (+34° C.) at the time when the second current is measured to, e.g., +30° C. The absolute value (6° C.) of the difference between the post-changed first temperature value (+24° C.) and the post-changed second temperature value (+30° C.), is equal to or smaller than the predetermined threshold value (8° C.). Note that if the absolute value of the difference between the post-changed first temperature value and the post-changed second temperature value, is equal to or smaller than the predetermined threshold value, the post-changed first temperature value may be a value excluding +24° C., and the post-changed second temperature value may also be a value excluding +30° C.

In step S08B of FIG. 15, the calculation unit 53 corrects the first current value at the time when the second current is measured on the basis of the post-changed first temperature value, and also corrects the concentration value of the specified substance in the second sample on the basis of the post-changed second temperature value. The explanation of the correction of the first current value at the time when the second current is measured is the same as the explanation of step S08 of the processing flow illustrated in FIG. 13. Furthermore, the explanation of how the concentration value of the specified substance in the second sample is corrected, is the same as the explanation of step S08A of the processing flow illustrated in FIG. 14.

In step S09B of FIG. 15, the calculation unit 53 refers to the post-corrected concentration value of the specified substance in the second sample, and calibrates the post-corrected first current value to the concentration value of the specified substance in the first sample. Herein, an in-depth description of the process in step S09B of FIG. 15 will be given. At first, the calculation unit 53 selects the calibration curve data corresponding to the post-changed first temperature value from within the plural sets of calibration curve data stored in the storage unit 56. Then, the calculation unit 53 calculates the concentration value of the specified substance in the first sample by applying the post-corrected first current value to the selected calibration curve data.

Next, the calculation unit 53 modifies the post-calculated concentration value of the specified substance in the first sample in a manner that refers to the post-corrected concentration value of the specified substance in the second sample. In the case of finishing the process in step S09B of FIG. 15, the processing flow by the calculation unit 53 depicted in FIG. 15 is terminated. The processes in step S07B through step S09B of FIG. 15 are also termed the calibration process by the calculation unit 53 in the present specification.

The discussion made above demonstrates, in the processing flow depicted in FIG. 15, the example where if the difference information exceeds the predetermined threshold value (NO in step S05 of FIG. 15), the calculation unit 53 advances to the process in step S07B of FIG. 15. In place of this operation, in the processing flow depicted in FIG. 15, if the difference information exceeds the predetermined threshold value (NO in step S05 of FIG. 15), the calculation unit 53 may finish the processing flow illustrated in FIG. 15 without advancing to the process in step S07B of FIG. 15. That is, in the processing flow depicted in FIG. 15, if the difference information exceeds the predetermined threshold value (NO in step S05 of FIG. 15), the calibration process by the calculation unit 53 may not be executed.

<Display Process>

The calculation unit 53 continuously receives the first current values from the detection device 2 and also stores the first current values in the storage unit 56. The calculation unit 53 calibrates to the concentration value of the specified substance in the first sample from the first current value from and after the time when the second current is measured on the basis of the first current value at the time when the second current is measured and the post-calibrated concentration value of the specified substance in the first sample. Then, the calculation unit 53 displays, on the display unit 54, the post-calibrated concentration value of the specified substance in the first sample as a blood sugar level or a value indicating the concentration value of the specified substance in the sample taken out of the body. To be specific, the display unit 54 displays the post-calibrated concentration value of the specified substance in the first sample as the blood sugar level or the value indicating the concentration value of the specified substance in the sample taken out of the body. The display unit 54 of the display device 3 displays the measurement result of the detection device 2, thereby enabling the system user and the examinee to easily recognize the blood sugar level of the examinee.

Further, in the processing flow illustrated in FIG. 13, 14 or 15, if the difference information exceeds the predetermined threshold value (NO in step S05 of FIG. 13, 14 or 15), the calculation unit 53 may not display the post-calibrated concentration value of the specified substance in the first sample on the display unit 54. Namely, in the processing flow illustrated in FIG. 13, 14 or 15, if the difference information exceeds the predetermined threshold value (NO in step S05 of FIG. 13, 14 or 15), the display unit 54 may not display the post-calibrated concentration value of the specified substance in the first sample.

<Notifying Process>

The following discussion will deal with a condition of a notifying process by the notifying unit 55, i.e., timing when the notifying unit 55 notifies of predetermined information. Further, a specific content of the predetermined information will be discussed. Still further, the condition for the notifying process by the notifying unit 55 will be discussed. For example, in the processing flow illustrated in FIG. 13, 14 or 15, if the difference information exceeds the predetermined threshold value (NO in step S05 of FIG. 13, 14 or 15), the notifying unit 55 notifies of the predetermined information. The notifying unit 55 may display the predetermined information on the display unit 54. Moreover, the notifying unit 55 may notify of the predetermined information in voice by use of a voice output device.

Next, the specific content of the predetermined information will be discussed. The predetermined information is exemplified by information representing that the first temperature value at the time when the second current is measured is largely different from the second temperature value at the time when the second current is measured. The information indicating that the first temperature value at the time when the second current is measured is largely different from the second temperature value at the time when the second current is measured, is also referred to as first information in the present specification. The notifying unit 55 notifies of the first information, thereby enabling the user of the analysis system and the examinee to recognize that the first temperature value at the time when the second current is measured, is largely different from the second temperature value at the time when the second current is measured. In this case, the notifying unit 55 gives the notification of the first information, and concurrently the calibration process by the calculation unit 53 is executed.

Further, the predetermined information is exemplified by information indicating that the first temperature value at the time when the second current is measured is largely different from the second temperature value at the time when the second current is measured, and therefore the calibration cannot be conducted. The information indicating that the first temperature value at the time when the second current is measured is largely different from the second temperature value at the time when the second current is measured, and therefore the calibration cannot be conducted, is also termed second information in the present specification. The notifying unit 55 notifies of the second information, thereby enabling the user of the analysis system and the examinee to recognize that the calibration cannot be conducted. In this instance, the notifying unit 55 gives the notification of the second information, however, the calibration process by the calculation unit 53 does not be executed.

Moreover, the predetermined information is exemplified by information for prompting the user to measure again the second sample because of there being the large difference between the first temperature value at the time when the second current is measured and the second temperature value at the time when the second current is measured. The information for prompting the user to measure again the second sample because of there being the large difference between the first temperature value at the time when the second current is measured and the second temperature value at the time when the second current is measured, is also referred to as third information in the present specification. The notifying unit 55 notifies of the third information, thereby enabling the user of analysis system and the examinee to measure again the second sample. In this case, the notifying unit 55 gives the notification of the third information, however, the calibration process by the calculation unit 53 does not be executed.

The first working example has demonstrated the instance in which the display device 3 and the measuring device 4 are configured as the separate devices. The present embodiment may, without being limited to this configuration, take another configuration that the display device 3 and the measuring device 4 may be configured as one integral device. In this case, the display device 3 and the measuring device 4 may be configured in such a mode that the display device 3 is included as a part of the measuring device 4 or a mode that the measuring device 4 is included as a part of the display device 3.

Second Working Example

Figure 16:
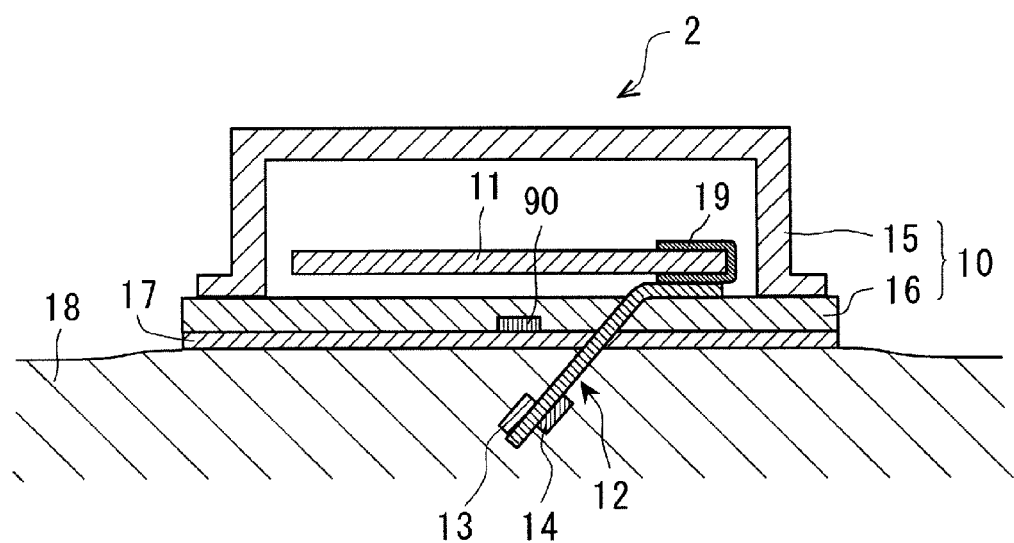
FIG. 16 is a schematic view of a configuration of the detection device 2 according to a second working example.

A second working example of the analysis system according to the present embodiment will be described. The first working example has demonstrated the instance where the electrochemical sensor 12 of the detection device 2 is provided with the temperature detection unit 14. The second working example will demonstrate an example in which the electrochemical sensor 12 of the detection device 2 is provided with the temperature detection unit 14, and a temperature detection unit 90 is provided in the interior of the detection device 2. FIG. 16 is a schematic view of a configuration of the detection device 2 according to the second working example. Note that the same components as those in the first working example are marked with the same numerals and symbols as those in the first working example, while the explanations thereof are omitted.

The detection device 2 includes the housing 10, the circuit board 11, the electrochemical sensor 12, the signal detection unit 13, the temperature detection unit 14 and further the temperature detection unit 90. Similarly to the first working example, the housing 10 includes the cover 15 and the substrate 16. The temperature detection unit 90 is provided in a notched portion of the substrate 16. In the case of disposing the temperature detection unit 90 in the notched portion of the substrate 16, a temperature detected by the temperature detection unit 90 is approximately coincident with the surface temperature of the skin 18. The location where the temperature detection unit 90 is disposed is not limited to the notched portion of the substrate 16 but may be, e.g., the upper surface and the undersurface of the housing 10, the upper surface and the undersurface of the circuit board 11 and the upper surface and the undersurface of the substrate 16. That is, the temperature detection unit 90 may be provided in an arbitrary location in the interior of the detection device 2.

The temperature detection unit 90 is connected to the circuit board 11 via the lead wires. The temperature values, which are continuously detected by the temperature detection unit 90, are transferred to the circuit board 11. The variety of known sensors in addition to, e.g., the thermistor can be employed as the temperature detection unit 90.

The temperature measuring unit 35 equipped in the detection device 2 compares the first temperature value detected by the temperature detection unit 14 with a temperature value detected by the temperature detection unit 90. Then, the temperature measuring unit 35 determines whether or not a predetermined range contains an absolute value of a difference between the first temperature value detected by the temperature detection unit 14 and the temperature value detected by the temperature detection unit 90. The predetermined range is stored in the storage unit 33. The predetermined range is defined by arbitrarily changeable values and can be set such as 1.0° C. through 3.0° C. or 1.5° C. through 2.0° C. but is not limited to these values.

If the predetermined range does not contain the absolute value of the difference between the first temperature value detected by the temperature detection unit 14 and the temperature value detected by the temperature detection unit 90, the temperature measuring unit 35 informs the notifying unit 55 of alarm information. For example, if the predetermined range ranges from 1.5° C. to 2.0° C. and if the absolute value of the difference between the first temperature value detected by the temperature detection unit 14 and the temperature value detected by the temperature detection unit 90 is 4.0° C. or 0.5° C., the temperature measuring unit 35 informs the notifying unit 55 of the alarm information. The notifying unit 55 receiving the alarm information gives the notification of the alarm information. The notifying unit 55 may display the alarm information on the display unit 54. Further, the notifying unit 55 may notify of the alarm information in voice by use of a voice output device. Moreover, the notifying unit 55 may notify of the alarm information in light by employing a light output device such as an alarm light.

The temperature measuring unit 35 can detect that the predetermined range does not contain the absolute value of the difference between the first temperature value detected by the temperature detection unit 14 and the temperature value detected by the temperature detection unit 90. That is, the temperature measuring unit 35 can detect de-insertion of the electrochemical sensor 12 off the skin 18 and a failure in insertion of the electrochemical sensor 12 into the skin 18. Then, the notifying unit 55 notifies of the alarm information, thereby enabling the user of the analysis system and the examinee to recognize the de-insertion of the electrochemical sensor 12 off the skin 18 and the failure in insertion of the electrochemical sensor 12 into the skin 18.

Third Working Example

Figure 17:
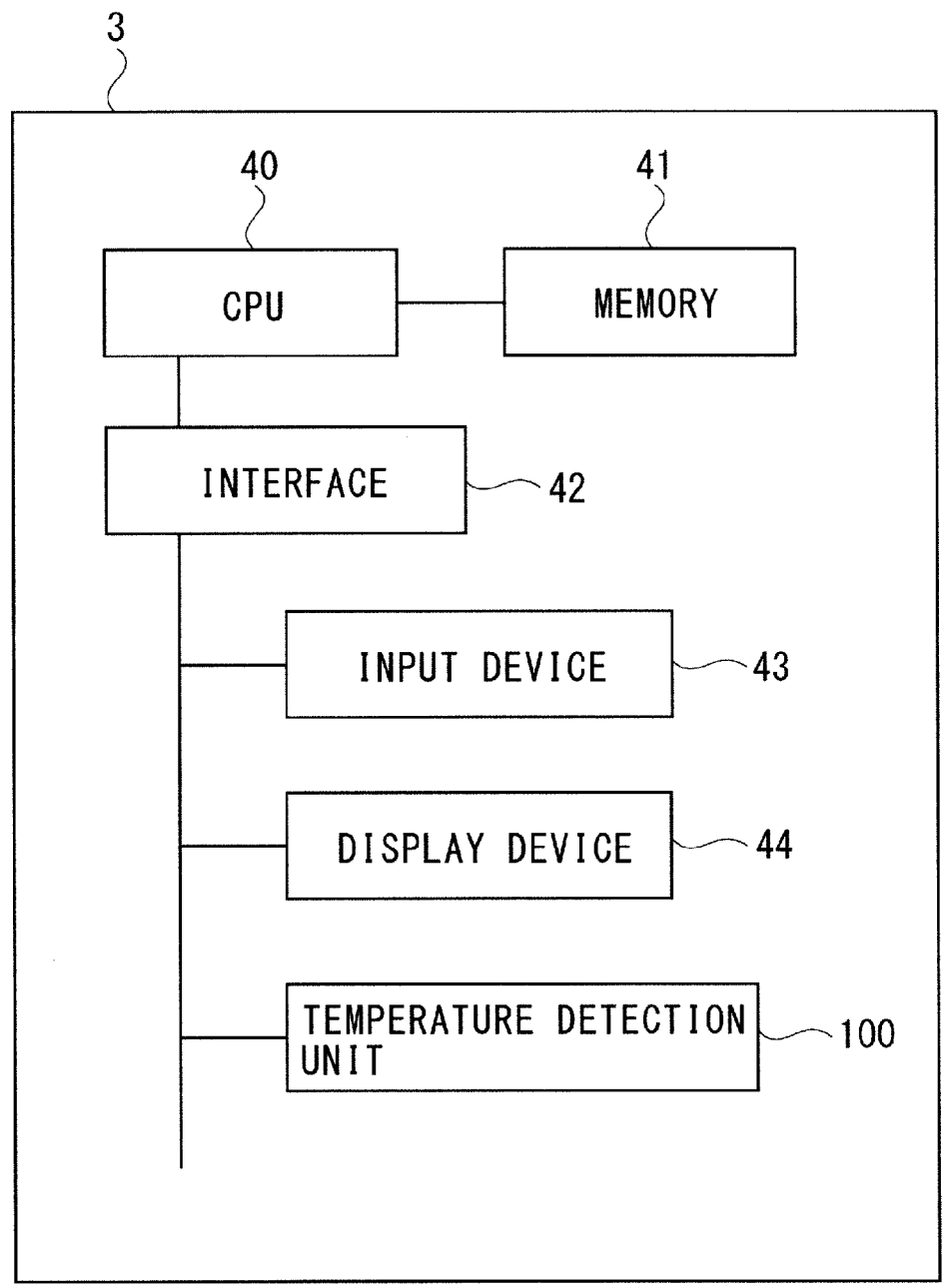
FIG. 17 is a schematic diagram of a configuration of the display device 3 according to a third working example.

A third working example of the analysis system according to the present embodiment will be described. The first and second working examples have demonstrated the example in which the measuring device 4 is provided with the temperature detection unit 66. The third working example will demonstrate an example where the measuring device 4 is provided with the temperature detection unit 66, and the display device 3 is provided with a temperature detection unit 100. FIG. 17 is a schematic view of a configuration of the display device 3 according to the third working example. Note that the same components as those in the first and second working examples are marked with the same numerals and symbols as those in the first and second working example, while the explanations thereof are omitted.

The display device 3 includes the CPU 40, the memory 41, the interface 42, the input device 43, the output device 44 and further the temperature detection unit 100. Temperature values, which are continuously detected by the temperature detection unit 100, are transferred to the CPU 40. The variety of known sensors in addition to, e.g., the thermistor can be used as the temperature detection unit 100.

The calculation unit 53 of the display device 3 stores, in the storage unit 56, the information on the variation of the temperature values detected by the temperature detection unit 100 together with the elapsed time information. The calculation unit 53 of the display device 3 may calibrate the measurement result of the first sample by the detection device 2 in a way that uses the temperature values detected by the temperature detection unit 100 in place of the second temperature values.

Moreover, the third working example has demonstrated the instance in which the measuring device 4 is provided with the temperature detection unit 66, and the display device 3 is provided with the temperature detection unit 100, however, the present embodiment is not confined to this configuration. In the present embodiment, the display device 3 may be provided with the temperature detection unit 100, while the measuring device 4 may not be provided with the temperature detection unit 66.

The first through third working examples have demonstrated the instance in which the calculation unit 53 of the display device 3 calibrates the measurement result, given by the detection device 2, of the first sample, however, the present embodiment is not confined to this configuration. The detection device 2 may include the same calculation unit as the calculation unit 53 of the display device 3. Then, the calculation unit of the detection device 2 may calibrate the measurement result, given by the detection device 2, of the first sample. The calculation unit of the detection device 2 can be realized by the computer including the CPU, the RAM and the ROM that are mounted on the circuit board 11 of the detection device 2, by a variety of devices and by the programs executed on the computer. Further, the measuring device 4 may include the same calculation unit as the calculation unit 53 of the display device 3. Then, the calculation unit of the measuring device 4 may calibrate the measurement result, given by the detection device 2, of the first sample. The calculation unit of the measuring device 4 can be realized by the computer including the CPU 40, the memory 41, and so forth equipped in the measuring device 4, by a variety of devices and by the programs executed on the computer. Further, the wireless or wired data communications may also be performed between the detection device 2 and the measuring device 4.

The discussion has proceeded so far in such a manner that the first through third working examples have exemplified the analysis system equipped with the detection device 2, the display device 3 and the measuring device 4, however, the present embodiment is not limited to this analysis system. An analysis apparatus may be configured to include the detection device 2, the display device 3 and the measuring device 4. Further, an apparatus may be configured to include the detection device 2, the display device 3 and the measuring device 4 as one integral device.

In the present embodiment, the first sample is measured by use of the electrochemical sensor 12, and the second sample is measured by employing the electrochemical technique. Without being limited to the sensor and the technique described above, for instance, such a sensor and an optical technique may be used as to detect signal values pertaining to the quantities and the concentrations of the specified substances in the first sample and the second sample by detecting, e.g., reflected beams of light. Moreover, the present embodiment has discussed the example in which the body fluid of the person (examinee), the matrix containing liquid other than the body fluid, and so forth are used as the samples, however, other available samples may be body fluids of other subjects (e.g., animals excluding the human being), the matrix containing liquids excluding the body fluids, and so forth.

<Effect of Present Embodiment>

If there is no divergence equal to or larger than a fixed value between the ambient temperature at which the first sample is measured and the ambient temperature at which the second sample is measured, the measurement result of the first sample is calibrated. Accordingly, even if the ambient temperature at which the first sample is measured fluctuates largely and if the ambient temperature at which the second sample is measured fluctuates largely, the measurement result exhibiting high reliability can be acquired when measuring the first sample.

If there is the divergence equal to or larger than the fixed value between the ambient temperature at which the first sample is measured and the ambient temperature at which the second sample is measured, the measurement result of the first sample is calibrated by changing any one or both of the temperature value related to the first sample and the temperature value related to the second sample. Therefore, even if the ambient temperature at which the first sample is measured fluctuates largely and if the ambient temperature at which the second sample is measured fluctuates largely, the measurement result exhibiting the high reliability can be acquired when measuring the first sample.

<<Description Relating to Computer-Readable Medium>>

Any of the functions of the embodiment described above may be encoded and stored in a storage area of a computer-readable medium. In this case, a program for realizing the function may be provided to the computer, or to a computer incorporated into a machine or an apparatus, via the computer-readable medium. The function can be realized by having the computer, or the computer incorporated into a machine or an apparatus, read the program from the storage area of the computer-readable medium and execute the program.

Here, the computer-readable medium denotes a recording medium that employs an electric, magnetic, optical, chemical, physical, or mechanical action to accumulate information such as programs and data and holds the information in a condition that allows reading thereof to a computer. A flexible disk, a magneto-optical disk, a CD-ROM, a CD-R/W, a DVD, a DAT, 8 mm tape, a memory card, and so on may be cited as examples of recording media that can be attached to and detached from a computer. Further, a hard disk, a ROM, and so on may be cited as recording media that are fixed to a computer.

DESCRIPTION OF THE REFERENCE NUMERALS AND SYMBOLS 1 analysis system
2 detection device
3 display device
4 measuring device
12 electrochemical sensor
13 signal detection unit
14, 66, 99, 100 temperature detection unit
30, 50, 80 communication unit
31, 51, 81 power unit
32, 52, 82 control unit
33, 56, 84 storage unit
53 calculation unit
54 display unit
55 notifying unit
83 measuring unit

The invention claimed is:

1. An analysis apparatus comprising:
an electrochemical sensor positioned subcutaneously and configured to continuously detect signal values from a first sample where the first sample is an extracellular fluid in a subject's body comprising a specified substance, the electrochemical sensor comprising:
 a first temperature detection unit configured to capture a first temperature value defined as temperature information for the extracellular fluid,
 a signal detection unit, and
 a substrate,
wherein the signal detection unit comprises:
 a working electrode and a counter electrode formed on a surface of the substrate, and
 a reagent layer, where the reagent layer is immobilized on the working electrode, the reagent layer comprising an oxidation reduction enzyme and an electron transfer substance;
a measuring unit configured to measure numerical value information for the specified substance present in a second sample where the second sample is blood from the subject outside the subject's body;
a second temperature detection unit configured to capture a second temperature value defined as temperature information for the blood; and
a calculation unit configured to calibrate numerical value information for the specified substance in the extracellular fluid from the signal value by referring to the numerical value information for the specified substance in the blood in accordance with the first temperature value and the second temperature value,
wherein:
 the calculation unit is further configured to acquire a first temperature acquired value defined as the first temperature value at the time when the numerical value information for the specified substance in the blood is measured,
 the calculation unit is further configured to acquire a second temperature acquired value defined as the second temperature value at the time when the numerical value information for the specified substance in the blood is measured, and when a value calculated for the first temperature acquired value and the second temperature acquired value is equal to or less than a predetermined threshold value, the calculation unit is configured to calibrate the numerical value information for the specified substance in the extracellular fluid from the signal value by referring to the numerical value information for the specified substance in the blood, whereas when the value calculated for the first temperature acquired value and the second temperature acquired value exceeds the predetermined threshold value, the calculation unit is not configured to calibrate the numerical value information for the specified substance in the extracellular fluid from the signal value, with the result that a user of the analysis apparatus is notified by a notifying unit when the calibration of the numerical value information was executed and when the calibration was not executed.

2. The analysis apparatus according to claim 1, wherein when a value calculated from the first temperature acquired value and the second temperature acquired value exceeds a predetermined threshold value, the calculation unit is configured to change the first temperature acquired value, to correct the signal value detected from the extracellular fluid on the basis of the post-changed first temperature acquired value when a value calculated from the post-changed first temperature acquired value and the second temperature acquired value is equal to or less than the predetermined threshold value, and to calibrate the numerical value information for the specified substance in the extracellular fluid from the post-corrected signal value by referring to the numerical value information for the specified substance in the blood.

3. The analysis apparatus according to claim 1, wherein when a value calculated from the first temperature acquired value and the second temperature acquired value exceeds a predetermined threshold value, the calculation unit is configured to change the second temperature acquired value, to correct the numerical value information for the specified substance in the blood on the basis of the post-changed second temperature acquired value when a value calculated from the first temperature acquired value and the post-changed second temperature acquired value is equal to or less than the predetermined threshold value, and to calibrate the numerical value information for the specified substance in the extracellular fluid from the signal value by referring to the post-corrected numerical value information for the specified substance in the blood.

4. The analysis apparatus according to claim 1, wherein when a value calculated from the first temperature acquired value and the second temperature acquired value exceeds a predetermined threshold value, the calculation unit is configured to change the first temperature acquired value and the second temperature acquired value, to correct the signal value detected from the extracellular fluid on the basis of the post-changed first temperature acquired value when a value calculated from the post-changed first temperature acquired value and the post-changed second temperature acquired value is equal to or less than the predetermined threshold value, to further correct the numerical value information for the specified substance in the blood on the basis of the post-changed second temperature acquired value, and to calibrate the numerical value information for the specified substance in the extracellular fluid from the post-corrected signal value by referring to the post-corrected numerical value information for the specified substance in the blood.

5. An analysis method comprising:
a step of continuously detecting signal values by a subcutaneously positioned electrochemical sensor from a first sample where the first sample is an extracellular fluid in a subject's body comprising a specified substance, the electrochemical sensor comprising:
 a first temperature detection unit configured to capture a first temperature value defined as temperature information for the extracellular fluid,
 a signal detection unit, and
 a substrate,
wherein the signal detection unit comprises:
 a working electrode and a counter electrode formed on a surface of the substrate, and
 a reagent layer, where the reagent layer is immobilized on the working electrode, the reagent layer comprising an oxidation reduction enzyme and an electron transfer substance;
a measuring step of measuring numerical value information by a measuring unit for the specified substance present in a second sample where the second sample is blood from the subject outside the subject's body;
a second temperature detecting step of capturing a second temperature value by a second temperature detection unit, where second temperature value is defined as temperature information for the blood; and
a calculating step of calibrating to the numerical value information by a calculation unit for the specified substance in the extracellular fluid from the signal value by referring to the numerical value information for the specified substance in the blood in accordance with the first temperature value and the second temperature value,
wherein the calculating step comprises:
 acquiring a first temperature acquired value defined as the first temperature value at the time when measuring the numerical value information for the specified substance in the blood,
 acquiring a second temperature acquired value defined as the second temperature value at the time when measuring the numerical value information for the specified substance in the blood, and
 calibrating the numerical value information for the specified substance in the extracellular fluid from the signal value by referring to the numerical value information for the specified substance in the blood when a value calculated from the first temperature acquired value and the second temperature acquired value is equal to or less than a predetermined threshold value, whereas when the value calculated from the first temperature acquired value and the second temperature acquired value exceeds the predetermined threshold value, the calculating step does not include calibrating the numerical value information for the specified substance in the extracellular blood from the signal value, and
 providing notification when the calibration of the numerical value information was executed and when the calibration was not executed.

6. The analysis method according to claim 5, wherein the calculating step further comprises changing the first temperature acquired value when a value calculated from the first temperature acquired value and the second temperature acquired value exceeds a predetermined threshold value, correcting the signal value detected from the extracellular fluid on the basis of the post-changed first temperature acquired value when a value calculated from the post-changed first temperature acquired value and the second temperature acquired value is equal to or less than the predetermined threshold value, and calibrating the numerical value information for the specified substance in the extracellular fluid from the post-corrected signal value by referring to the numerical value information for the specified substance in the blood.

7. The analysis method according to claim 5, wherein the calculating step further comprises:
changing the second temperature acquired value when a value calculated from the first temperature acquired value and the second temperature acquired value exceeds a predetermined threshold value,
correcting the numerical value information for the specified substance in the blood on the basis of the post-changed second temperature acquired value when a value calculated from the first temperature acquired value and the post-changed second temperature acquired value is equal to or less than the predetermined threshold value, and
calibrating the numerical value information for the specified substance in the extracellular fluid from the signal value by referring to the post-corrected numerical value information for the specified substance in the blood.

8. The analysis method according to claim 5, wherein the calculating step includes changing the first temperature acquired value and the second temperature acquired value when a value calculated from the first temperature acquired value and the second temperature acquired value exceeds a predetermined threshold value, correcting the signal value detected from the extracellular fluid on the basis of the post-changed first temperature acquired value when a value calculated from the post-changed first temperature acquired value and the post-changed second temperature acquired value is equal to or smaller than the predetermined threshold value, further correcting the numerical value information for the specified substance in the blood on the basis of the post-changed second temperature acquired value, and calibrating to the numerical value information for the specified substance in the
extracellular fluid from the post-corrected signal value by referring to the post-corrected numerical value information for the specified substance in the blood.

9. An analysis system comprising:
a detection device comprising:
an electrochemical sensor positioned subcutaneously and configured to continuously detect signal values from a first sample where the first sample is an extracellular fluid in a subject's body comprising a specified substance, the electrochemical sensor comprising:
a first temperature detection unit configured to capture a first temperature value defined as temperature information for the extracellular fluid,
a signal detection unit, and
a substrate,
wherein the signal detection unit comprises:
a working electrode, and a counter electrode formed on a surface of the substrate and
a reagent layer, where the reagent layer is immobilized on the working electrode, the reagent layer comprising an oxidation reduction enzyme and an electron transfer substance; and
an analysis device comprising:
a measuring unit configured to measure numerical value information for a specified substance present in a second sample where the second sample is blood outside the subject's body; and
a second temperature detection unit configured to capture a second temperature value defined as temperature information for the blood;
a display device comprising:
a display unit configured to display the numerical value information for a specified substance in the extracellular fluid; and
a calculation unit configured to calibrate the numerical value information for the specified substance in the extracellular fluid from the signal value detected from the extracellular fluid by referring to the numerical value information for the specified substance in the blood;
wherein:
the calculation unit is further configured to acquire a first temperature acquired value defined as the first temperature value at the time when measuring the numerical value information for the specified substance in the blood,
the calculation unit is further configured to acquire a second temperature acquired value defined as the second temperature value at the time when measuring the numerical value information for the specified substance in the blood, and
when a value calculated from the first temperature acquired value and the second temperature acquired value is equal to or less than a predetermined threshold value, the calculation unit is configured to calibrate the numerical value information for the specified substance in the extracellular fluid from the signal value by referring to the numerical value information for the specified substance in the blood, whereas
when the value calculated from the first temperature acquired value and the second temperature acquired value exceeds the predetermined threshold value, the calculation unit is not configured to calibrate the numerical value information for the specified substance in the extracellular fluid from the signal value,
with the result that a user of the analysis system is notified by a notifying unit when the calibration of the numerical value information was executed and when the calibration was not executed.

10. The analysis system according to claim 9, wherein the calculation unit is configured to change the first temperature acquired value when a value calculated from the first temperature acquired value and the second temperature acquired value exceeds a predetermined threshold value, to correct the signal value detected from the extracellular fluid on the basis of the post-changed first temperature acquired value when a value calculated from the post-changed first temperature acquired value and the second temperature acquired value is equal to or less than the predetermined threshold value, and to calibrate the numerical value information for the specified substance in the extracellular fluid from the post-corrected signal value by referring to the numerical value information for the specified substance in the blood.

11. The analysis system according to claim 9, wherein the calculation unit is configured to change the second temperature acquired value when a value calculated from the first temperature acquired value and the second temperature acquired value exceeds a predetermined threshold value, to correct the numerical value information for the specified substance in the blood on the basis of the post-changed second temperature acquired value when a value calculated from the first temperature acquired value and the post-changed second temperature acquired value is equal to or less than the predetermined threshold value, and to calibrate the numerical value information for the specified substance in the extracellular fluid from the signal value by referring to the post-corrected numerical value information for the specified substance in the blood.

12. The analysis system according to claim 9, wherein the calculation unit is configured to change the first temperature acquired value and the second temperature acquired value when a value calculated from the first temperature acquired value and the second temperature acquired value exceeds a predetermined threshold value, to correct the signal value detected from the extracellular fluid on the basis of the post-changed first temperature acquired value when a value calculated from the post-changed first temperature acquired value and the post-changed second temperature acquired value is equal to or less than the predetermined threshold value, to further correct the numerical value information for the specified substance in the blood on the basis of the post-changed second temperature acquired value, and to calibrate the numerical value information for the specified substance in the extracellular fluid from the post-corrected signal value by referring to the post-corrected numerical value information for the specified substance in the blood.

13. The analysis apparatus according to claim 1, further comprising a notifying unit configured to notify when a value calculated from the first temperature value and the second temperature value exceeds the predetermined threshold value of information indicating that the calculated value exceeds the predetermined threshold value.

14. The analysis method according to claim 5, further comprising a notifying step of notifying when a value calculated from the first temperature value and the second temperature value exceeds the predetermined threshold value of information indicating that the calculated value exceeds the predetermined threshold value.

15. The analysis system according to claim 9, wherein the display unit is configured to notify when a value calculated from the first temperature value and the second temperature value exceeds the predetermined threshold value of information indicating that the calculated value exceeds the predetermined threshold value.

\* \* \* \* \*